United States Patent
Altshuler et al.

(10) Patent No.: US 7,223,281 B2
(45) Date of Patent: May 29, 2007

(54) MULTI-DIRECTIONAL ORAL PHOTOTHERAPY APPLICATOR

(76) Inventors: Gregory B. Altshuler, 137 Marion St., Wilmington, MA (US) 01887; Valery V. Tuchin, 32/34 Volskaya Street Apartment 17, Saratov 410600 (RU)

( * ) Notice: Subject to any disclaimer, the term of this patent is extended or adjusted under 35 U.S.C. 154(b) by 0 days.

(21) Appl. No.: 10/776,686

(22) Filed: Feb. 10, 2004

(65) Prior Publication Data

US 2004/0193235 A1   Sep. 30, 2004

Related U.S. Application Data

(63) Continuation-in-part of application No. 10/680,705, filed on Oct. 7, 2003, and a continuation-in-part of application No. 10/702,104, filed on Nov. 4, 2003, which is a continuation-in-part of application No. 09/996,662, filed on Nov. 29, 2001, now Pat. No. 6,648,904.

(60) Provisional application No. 60/446,300, filed on Feb. 10, 2003, provisional application No. 60/446,342, filed on Feb. 10, 2003, provisional application No. 60/449,188, filed on Feb. 21, 2003.

(51) Int. Cl.
*A61N 5/01* (2006.01)

(52) U.S. Cl. .............................. 607/90; 607/88; 607/94

(58) Field of Classification Search ................. 433/29; 607/88–89
See application file for complete search history.

(56) References Cited

U.S. PATENT DOCUMENTS

| | | | |
|---|---|---|---|
| 1,590,283 A | 6/1926 | Catlin | |
| 3,261,978 A | 7/1966 | Brenman | |
| 3,667,454 A | 6/1972 | Prince | |
| 4,333,197 A | 6/1982 | Kuris | |
| 4,736,745 A * | 4/1988 | Gluckman | 606/15 |
| 4,784,135 A | 11/1988 | Blum et al. | |
| 4,840,174 A * | 6/1989 | Gluckman | 606/15 |
| 4,852,549 A * | 8/1989 | Mori | 607/92 |
| 4,862,903 A * | 9/1989 | Campbell | 128/861 |

(Continued)

FOREIGN PATENT DOCUMENTS

CN   1073607 A   6/1993

(Continued)

OTHER PUBLICATIONS

Shumilovitch et al, "Influence Of Low Intensity Laser Radiation Upon The Microfobia Of Carious Cavities And Root Canal," SPIE vol. 1984, pp. 215-220.

(Continued)

*Primary Examiner*—Henry M Johnson, III
(74) *Attorney, Agent, or Firm*—Thomas J. Engellenner; Reza Mollaaghababa; Nutter, McClennen & Fish LLP

(57) ABSTRACT

Oral phototherapy applicators are disclosed that are sized and shaped so as to fit at least partially in a user's mouth and have at least one radiation emitting element coupled to an apparatus body to irradiate a portion of the oral cavity with phototherapeutic radiation along multiple directions. In one aspect, the apparatus is configured to direct radiation to at least one portion of the oral cavity, such as the teeth, cheeks, tongue, palate, throat, lymphatic tissue, blood, glands, follicles, collagen, pigmentation or facial tissue, generally. The apparatus can further include bristles to provide a phototherapeutic toothbrush. Alternatively, the apparatus body can be adapted for placement in a fixed position relative to the oral cavity during phototherapy.

39 Claims, 19 Drawing Sheets

U.S. PATENT DOCUMENTS

| | | | |
|---|---|---|---|
| 4,930,504 | A | 6/1990 | Diamantopoulos et al. |
| 5,030,090 | A | 7/1991 | Maeda et al. |
| 5,133,102 | A * | 7/1992 | Sakuma .................... 15/167.1 |
| 5,171,564 | A | 12/1992 | Nathoo et al. |
| 5,293,880 | A * | 3/1994 | Levitt ......................... 128/861 |
| 5,300,097 | A | 4/1994 | Lerner et al. |
| 5,342,358 | A | 8/1994 | Daikuzono |
| 5,369,831 | A | 12/1994 | Bock |
| 5,445,608 | A * | 8/1995 | Chen et al. ................... 604/20 |
| 5,536,168 | A * | 7/1996 | Bourke .......................... 433/6 |
| 5,561,881 | A | 10/1996 | Klinger et al. |
| 5,611,793 | A | 3/1997 | Wilson et al. |
| 5,616,140 | A | 4/1997 | Prescott |
| 5,658,148 | A | 8/1997 | Neuberger et al. |
| 5,673,451 | A | 10/1997 | Moore et al. |
| 5,974,616 | A | 11/1999 | Dreyfus |
| 6,026,828 | A | 2/2000 | Altshuler |
| 6,029,303 | A * | 2/2000 | Dewan ........................ 15/105 |
| 6,029,304 | A | 2/2000 | Hulke et al. |
| 6,056,548 | A | 5/2000 | Neuberger et al. |
| 6,086,363 | A | 7/2000 | Moran et al. |
| 6,094,767 | A * | 8/2000 | Iimura ........................ 15/105 |
| 6,106,294 | A | 8/2000 | Daniel |
| 6,126,655 | A * | 10/2000 | Domankevitz et al. ....... 606/17 |
| 6,135,774 | A | 10/2000 | Hack et al. |
| 6,162,055 | A | 12/2000 | Montgomery et al. |
| 6,239,442 | B1 * | 5/2001 | Iimura .................... 250/504 R |
| 6,273,884 | B1 * | 8/2001 | Altshuler et al. .............. 606/9 |
| 6,290,496 | B1 | 9/2001 | Azar et al. |
| 6,343,933 | B1 | 2/2002 | Montgomery et al. |
| 6,387,353 | B1 | 5/2002 | Jensen et al. |
| 6,443,978 | B1 * | 9/2002 | Zharov ........................ 607/91 |
| 6,471,716 | B1 | 10/2002 | Pecukonis |
| 6,503,486 | B2 | 1/2003 | Xu et al. |
| 6,862,771 | B1 * | 3/2005 | Muller ........................ 15/105 |
| 2001/0024777 | A1 * | 9/2001 | Azar et al. .................... 433/29 |
| 2002/0018754 | A1 | 2/2002 | Sagel et al. |
| 2002/0081555 | A1 | 6/2002 | Wiesel |
| 2004/0143920 | A1 | 7/2004 | Nanda |

FOREIGN PATENT DOCUMENTS

| | | |
|---|---|---|
| DE | 198 03 460 C1 | 8/1999 |
| EP | 0 324 120 A1 | 7/1989 |
| EP | 0 593 375 A1 | 10/1992 |
| EP | 0 563 953 A2 | 4/1993 |
| EP | 0 743 029 | 11/1996 |
| EP | 0 927 544 A2 | 7/1999 |
| GB | 1 546 625 | 5/1979 |
| JP | 2174804 A2 | 7/1990 |
| JP | 6022871 A2 | 2/1994 |
| JP | 10014661 A2 | 1/1998 |
| WO | WO 88/04592 | 6/1988 |
| WO | WO 95/10243 | 4/1995 |
| WO | WO 98/06456 | 2/1998 |
| WO | WO 98/58595 | 12/1998 |
| WO | WO 99/43387 | 2/1999 |
| WO | WO 99/10046 | 3/1999 |
| WO | WO 99/62472 | 12/1999 |
| WO | WO 00/74583 | 12/2000 |
| WO | WO 02/094116 | 11/2002 |
| WO | WO 04/073537 | 9/2004 |
| WO | WO 04/084752 | 10/2004 |

OTHER PUBLICATIONS

Sandford et al., Thermal Effects During Desensitisation of Teeth with Gallium-Aluminum-Arsenide Lasers, University of Queensland Dental School, Periodontology 1994; 15:25-30.

Forrest-Winchester et al., The Effect of Infrared Laser Radiation on Dentinal Permeability in vitro, Department of Dentistry, University of Queensland Dental School, pp. 1-8, 1992.

Powell, "Laser Dental Decay Prevention: does it have a future?" SPIE vol. 3192, 1997.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Flouride Treatment," The Journal of Clinical Pediatric Dentistry, vol. 20, No. 1 pp. 9-13, 1995.

Oleinik, et al., "Automatized Securing Definition for Laser Therapy Indications in Case of Non-complicated Caries," SPIE, vol. 1984, pp. 238-244.

Kazmina, et al., "Laser Prophiaxis and Treatment of Primary Caries," SPIE vol. 1984, pp. 231-233.

Sokolova, et al., "Low-intense Laser Radiation in Complex Treatment of Inflammatory Diseases of Parodontium," SPIE vol. 1984, pp. 234-237.

Petrischev, et al. Clinical and Experimental Low-Intensive Laser Therapy in Dentistry, SPIE, vol. 1984, pp. 212-214.

Mamedova, et al., Microbiological Estimate of Parodontis Laser Therapy Efficiency, SPIE vol. 1984, pp. 247-249.

Kozlov, et al., "Lasers in Diagnostics and Treatment of Microcirculation Disorders Under Parodontitis," SPIE vol. 1984, pp. 253-264.

Kalivradzhiyan, et al., "The Usage of Low Intensity Laser Radiation for the Treatment of the Inflammatory processes of the Oral Cavity Mucosa after Applying Removable Plate Dentures," SPIE vol. 1984 pp. 225-230.

Walsh, "Laser "Curettage": a Critical Analysis," Periodontology 14:4-12, 1993.

Ozawa, et al., "Stimulatory Effects of Low-Power Laser Irradiation on Bone Formation in vitro," SPIE vol. 1984, pp. 281-288.

Shimizu, et al., "Prospect of Relieving Pain Due to Tooth Movement During Orthodontic Treatment Utilizing a GA-Al-As Diode Laser," SPIE vol. 1984, pp. 275-280.

Petrischev, et al., Report on Low Intensity Laser Radiation Usage in Dentistry, SPIE vol. 1984, pp. 202-211.

Karu, Photobiological Fundamentals of Low-Power Laser Therapy, 8th Congress of International Society for Laser Surgery and Medicine, Mar. 30, 1987.

Schindl, "Does Low Intensity Laser Irradiation Really Cause Cell Damage?" Lasers in Surgery and Medicine vol. 22, pp. 105, 2001.

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Karu, "Cell Attachment to Extracellular Matrices is Modulated by Pulsed Radiation at 820 nm and Chemicals that Modify the Activity of Enzymes in the Plasma Membrane," Lasers in Surgery and Medicine, vol. 29, pp. 274-281, 2001.

Maegawa, et al., "Effects of Near-Infrared Low-Level Laser Irradiation on Microcirculation," Lasers in Surgery and Medicine, vol. 27, pp. 427-437, 2000.

Van Breugel, "Power Density and Exposure Time of He-Ne Laser Irradiation Are More Important Than Total Energy Dose in Photo-Biomodulation of Human Fibroblasts in Vitro," Lasers in Surgery and Medicine, vol. 12 pp. 528-537, 1992.

Mang, "Effect of Soft Laser Treatment on Wound Healing in the Hamster Oral Mucosa," American Society for Laser Medicine and Surgery Abstracts, Chapters 25, pp. 5-8.

Altshuler, et al., "Modern Optics and Dentistry," Laser in Dentistry, pp. 283-297, 1995.

Altshuler, et al., "New Optical Effects in the Human Hard Tooth Tissues," Lasers and Medicine, Proc. SPIE vol. 1353, pp. 97-102, 1989.

Altshuler, et al., "Human Tooth as an Optical Device," SPIE vol. 1429 Holography and Interferometry and Optical Pattern Recognition in Biomedicine, pp. 95-104, 1991.

Ohbayashi, "Stimulatory Effect of Laser Irradiation on Calcified Nodule Formation in Human Dental Pulp Fibroblasts," ABSTRACT J-Endod. Jan. 1999; 25(1): 30-3.

Orchardson, "Effect of Pulsed Nd:YAG Laser Radiation on Action Potential Conduction in Nerve Fibres Inside Teeth in vitro," ABSTRACT J-Dent. Jul.-Aug. 1998; 26(5-6): 421-6.

Dabrowska, "Intravital Treatment of the Pulp with Stimulation Laser Biostimulation," ABSTRACT Rocz-Akad-Med-Bialymst. 1997; 42(1): 168-76.

Sing, "Electroacupuncture and Laser Stimulation Treatment: Evaluation by Somatosensory Evoked Potential in Conscious Rabbits," ABSTRACT AM-J-Chin-Med. 1997; 25(3-4): 263-71.

Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.

Dialog Abstract (English Language) of DE 1920803460, Hauptmann, G., et al.

* cited by examiner

| No. | AGENT | REFRACTIVE INDEX AT 589 nm | pH |
|---|---|---|---|
| 1 | GLUCOSE-18% | 1.348 | 6.3 |
| 2 | GLUCOSE-30% | 1.364 | 6.0 |
| 3 | GLYCEROL | 1.452 | 6.5 |
| 4 | PROPYLENE GLYCOL | 1.431 | 7.2 |
| 5 | VEROGRAFIN-76% | 1.485 | 7.2 |
| 6 | INTERSTITIAL LIQUID | 1.345 | 7.1 |
| 7 | COLLAGEN FIBERS | 1.457 | - |

MULTI-DIRECTIONAL ORAL PHOTOTHERAPY APPLICATOR

PRIORITY

This Application claims the benefit of priority to U.S. Provisional Application Ser. Nos. 60/446,300, filed Feb. 10, 2003 entitled "Light Emitting Toothbrush and Method of Its Application for Oral Bacteria Reduction and Periodontal Disease and Caries Lesion Treatment and Prevention;" 60/446,342, filed Feb. 10, 2003 entitled "Light Emitting Toothbrush and Method of Its Application for Tooth Whitening and Brightening;" 60/449,188, filed Feb. 21, 2003 entitled "Method and Apparatus for Rejuvenation of Hard and Soft Oral Tissue and Perioral Facial Skin and for Prevention and Healing of Diseases Thereof;" and claims priority as a continuation-in-part to U.S. Utility Application Ser. No. 10/680,705, filed Oct. 7, 2003 entitled "Methods and Apparatus for Performing Photobiostimulation" (currently pending), and Ser. No. 10/702,104, filed Nov. 4, 2003 entitled "Methods and Apparatus for Delivering Low Power Optical Treatments" (currently pending), which is a continuation-in-part of U.S. Utility Ser. No. 09/996,662 (now U.S. Pat. No. 6,648,904), filed Nov. 29, 2001 entitled "Methods and Apparatus for Controlling the Temperature of a Surface."

BACKGROUND OF THE INVENTION

The present invention relates to methods and apparatus for treating the oral cavity, including light emitting oral appliances such as light emitting toothbrushes and light emitting mouthpieces.

There are a wide spectrum of bacteria and other microorganisms found in the oral cavity. Although the presence of microorganisms does not indicate an unhealthy condition, if not attended to these microorganisms will cause a variety of undesirable effects including oral disease and cosmetic degradation. Tooth discoloration, caries formation, periodontitis and tooth loss are all possible results.

Oral bacteria creates plaque, a sticky, colorless film of bacteria on the surfaces of teeth and other tissue, and these plaque forming bacteria create toxins. Over time the plaque begins combining with other materials and hardens into a rough, porous deposit, calculus. The eventual result is gingival irritation (gingivitis) symptomized by gum swelling, bleeding, and fibrous enlargement of the gingival. In addition, the growth of plaque and calculus can cause the gums to move away from the teeth, resulting in pockets between the teeth and gums where bacteria can thrive. The bacteria toxins can also destroy gum tissue and even lead to bone loss.

Thus, the prevention and treatment of periodontal gum disease and early caries requires effective bacteria killing or growth suppression within all regions of the oral cavity. In particular, bacteria killing within the junction of gingival tissue and tooth root surface and under the enamel surface is important, as well as, difficult using traditional means.

Application of available, on the market, toothbrushes, toothpastes, mouth rinsing solutions and/or mouth irrigators containing chemical antibacterial agents, for prevention of periodontal disease is only partly successful. In addition, once tissue damage has started, conventional treatments are not effective at reversing the results.

In addition, the oral cavity can host a variety of other conditions which may or may not be a direct result of bacterial growth, including, tongue diseases, inflammation of salivary glands and small sublingual ducts, damaged nerves, oral pain, sore throat/tonsillitis, tooth hypersensitivity, and tooth discoloration. These conditions and others would benefit from a novel oral treatment regimen.

Thus, there is a need in the art for improved oral treatments which can effectively kill and/or suppress microorganisms, help to reverse the damaging effects of bacteria, and/or provide treatment for conditions in, near, or related to the oral cavity.

SUMMARY OF THE INVENTION

The present invention provides methods and apparatus for treating tissue in, through, or around the oral cavity. The invention further includes light emitting oral applicators for performing phototherapy in the oral cavity.

In one aspect, the invention provides an oral phototherapy applicator having a body sized and shaped so as to fit at least partially within a user's oral cavity and includes at least one radiation emitting element for irradiating a portion of the oral cavity with phototherapeutic radiation. The applicator can be capable of emitting radiation in multiple distinct spectral bands, and/or radiating multiple areas within the oral cavity.

In further aspect of the invention, the oral applicator can be adapted to conform to the shape of at least a portion of the oral cavity. For example, the oral applicator body can be compliant to facilitate conformation to at least a portion of the oral cavity and/or can be adapted for positioning between a user's teeth and gums.

The oral applicator can optionally include a plurality of bristles that are substantially transparent to phototherapeutic radiation within at least one wavelength range. In one embodiment, the bristles can act as waveguides via optical coupling to a radiation emitter to receive and propagate radiation therefrom. The bristles can alternatively act to diffuse light based on an enhanced shape and/or a scattering agent disposed in the bristles to diffuse radiation. In addition, the bristles can have light refractive characteristics selected to inhibit light transmission to the oral cavity in the absence of contact between the bristle and a surface of the oral cavity.

In another aspect of the invention, the oral applicator can include an optical element for delivering radiation primarily to tissue other than teeth. For example, where the oral applicator includes bristles, the radiation can be emitted in a direction which is not parallel to the bristles.

In other aspects, the present invention provides methods of biostimulation by irradiating at least a portion of a subject's oral cavity with radiation having at least one selected wavelength component so as to induce a biostimulating effect. By way of example, the biostimulating effect can cause any of an increased blood and lymph microcirculation in the irradiated portion, activation of blood microcirculation in tooth pulp, increased local macrophage activity, increased fibroblast, osteoblast and odontoblast proliferation, killing of at least one of bacteria, fungi, and viruses in the oral cavity, normalization of the oral cavity pH, killing of viruses within the subject's blood microcirculatory system, light-induced destruction of selected metabolic blood components, reduction of gum bleeding, reduction of tooth hypersensitivity, pain reduction in teeth and throat, periodontal and bone regeneration, implant connection, remineralization of enamel, prevention of caries, root canal sterilization, inflammation prevention and periodontial disease prevention and healing. In a further embodiment, multiple treatments session of the radiation are administered so as to reach a selected total radiation dose and thereby provide biostimulation.

In a related aspect, the biostimulating effect is achieved by irradiating the oral cavity during multiple treatment sessions with a radiation power in range of about 1 mW/cm$^2$ to about 10 W/cm$^2$ so as to deposit a radiation dose in a range of about 1 Joules/cm$^2$ to about 1000 Joules/cm$^2$, and more preferably in a range of about 10 Joules/cm$^2$ to about 100 Joules/cm$^2$, in the irradiated tissue. The treatment sessions, each of which can last for about 10 seconds to about 1000 seconds, or longer if needed, can be repeated until a total therapeutic dose of radiation is reached.

In another aspect, the biostimulating radiation is primarily directed to soft tissue in the oral cavity, e.g., facial tissue. In some embodiments, the oral cavity is irradiated so as to deposit a dose of radiation below the facial skin dermatological or cosmetic condition, such as acne.

In another aspect, the present invention provides a method of dental treatment that includes applying non-toxic chromophores to the oral cavity and delivering a low dose of radiation to the chromophores during a session. The radiation can have a wavelength in the absorption band of the non-toxic chromophore and the dose can be lower than the power density to which the chromophore is normally responsive. In subsequent sessions, the step of applying radiation is repeated until the chromophore is activated. The chromophore is preferably a tooth whitening and brightening agent and/or an antimicrobial agent, which in one embodiment, is applied as a film having chromophores positioned therein. As an additional step, heat and/or an additional chromophore can be applied to the oral cavity.

In another aspect of the invention, the oral cavity is directly photobleached with optical radiation in a spectrum absorbed by endogenous photosensitizers. Preferably, the endogenous chromophores are tooth stains present in the dentine.

Further understanding of the invention can be obtained by reference to the following detailed description in conjunction with the associated drawings, described briefly below.

BRIEF DESCRIPTION OF THE DRAWINGS

The invention will be more fully understood from the following detailed description taken in conjunction with the accompanying drawings.

DETAILED DESCRIPTION OF THE INVENTION

The present invention generally relates to light emitting oral appliances used for irradiating a user's oral cavity to treat conditions in, through and/or related to the oral cavity. The oral appliances of the present invention can include, for example, a light emitting toothbrush, a light emitting mouth piece, or various other types of light emitting probes adapted for insertion into the oral cavity.

Figure 1:
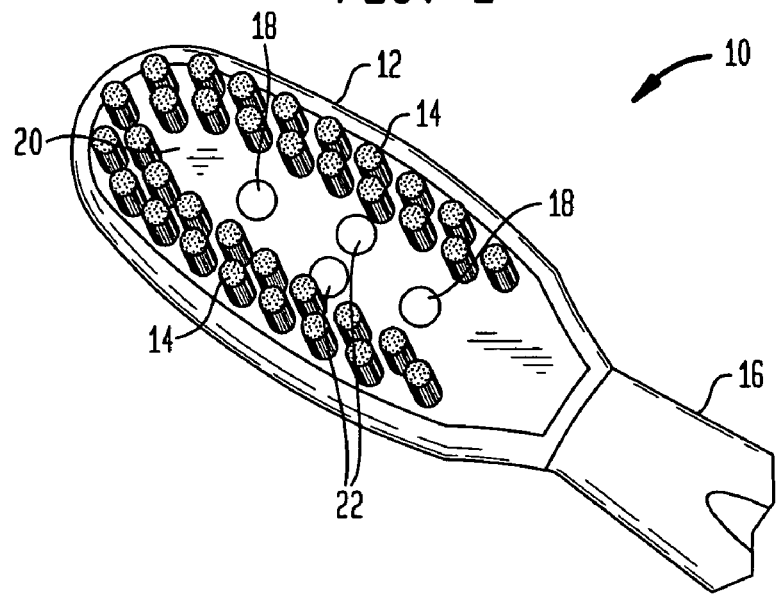
FIG. 1 illustrates a light emitting toothbrush of the present invention.
Figure 2A:
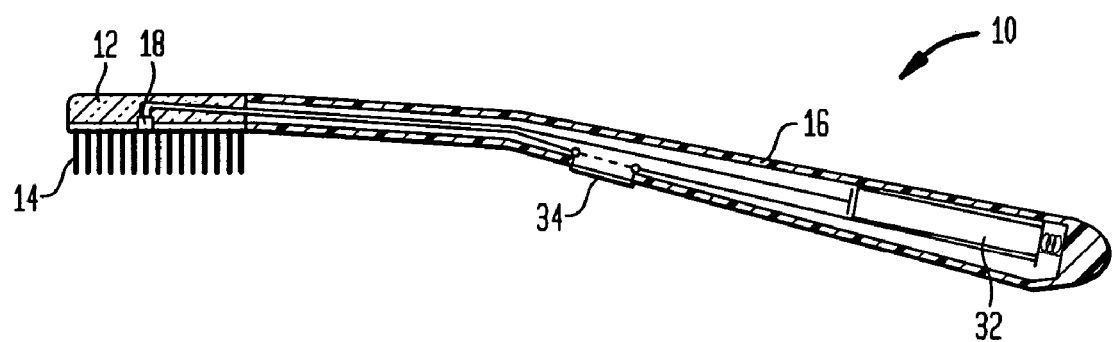
FIG. 2A illustrates another embodiment of the light emitting toothbrush of the present invention.
Figure 2B:
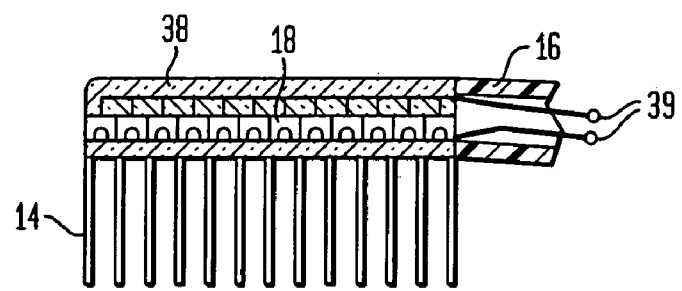
FIG. 2B is another view of the embodiment shown in FIG. 2A.

With reference to FIGS. 1, 2A, and 2B, one embodiment of a light emitting tooth brush (LETB) 10 according to the teachings of the invention includes a head portion (brush head) 12 with bristles 14, or other delivery system of optical energy, and a handle portion 16. The head portion preferably includes at least one optical radiation source 18 and can optionally include other features such as a highly reflective surface 20 and sensors 22. The optical radiation sources can also be mounted in the handle portion.

While in some embodiments, the head portion 12 and handle portion 16 can be optionally formed as a single unit, in other embodiments, the handle portion and the body portion are removably and replaceably mated with one another to allow cleaning and/or replacement. Handle portion 16 can include an electrical power supply 32, such as a battery, and a control switch 34 and optionally control electronics. FIG. 2B shows a more detailed view of head portion 12 including a frame 38 that can protect the internal components, and can be optionally formed of a thermally conductive material, such as, metal, ceramic, sapphire, high thermoconductive composite materials such as plastic with carbon fiber, to provide heat transfer from the light source 18 to an external environment. Head portion 12 can also include bristles 14 and leads 39 for supplying electrical power from the power supply 32 to optical radiation source 18.

As discussed in more detail below, the radiation source 18 can be a single source generating radiation either in a single bandwidth, or multiple distinct bandwidths. Alternatively, the radiation source 18 can include a plurality of light sources, for example, a matrix or an array of light emitting diodes (LED), generating radiation in similar or different bandwidths. The radiation source can be a multi-band light source, such as a multicolor LED. In some embodiments, the radiation source can be a broadband source, such as a lamp, and can be optionally coupled to one or more filters for selecting radiation within one or more desired bandwidths.

Figure 3:
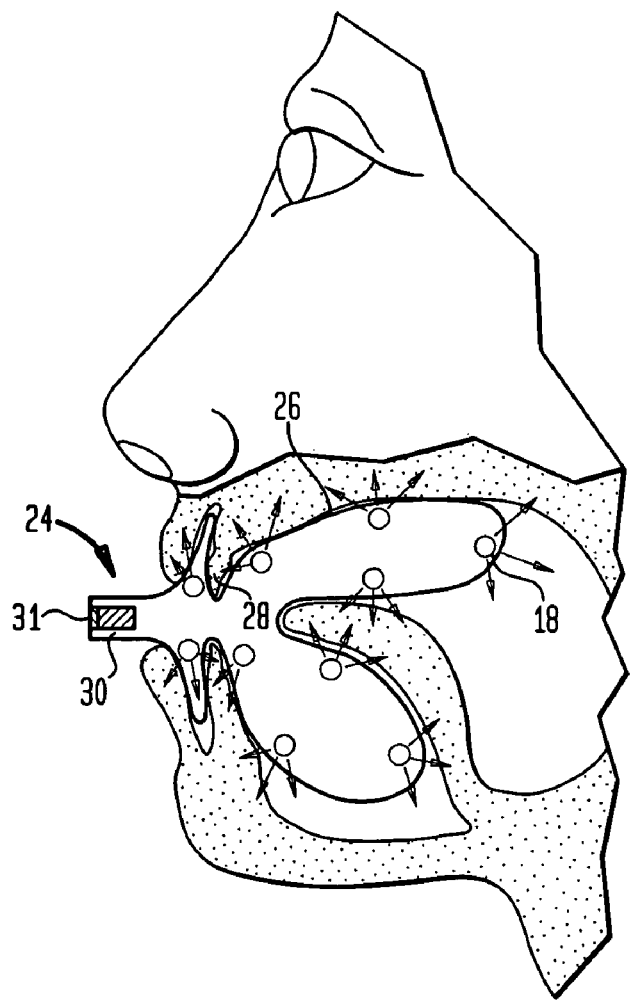
FIG. 3 illustrates a light emitting mouthpiece of the present invention.

FIG. 3 illustrates a light emitting mouthpiece (LEMP) 24 which includes a body portion 26 with optical radiation source 18. As shown, body portion 26 is sized and shaped to fit at least partially within a user's oral cavity. In addition, the body includes a surface shaped to conform to at least a portion of a user's oral cavity. In one embodiment, the light emitting mouthpiece can include a surface shaped for positioning against the teeth 28, including the incisors, bicuspids, and/or molars. The surface can also be formed to fit the portions of the oral cavity between the teeth and the walls of the oral cavity. Other body portions for which the surface can be adapted include a user's tongue, the roof of a user's mouth (hard and/or soft palate), and/or the floor of the oral cavity (for example, beneath a user's tongue).

Mouthpiece 24 can preferably include a handle 30 which allows a user to grip the mouthpiece, and can contain an electrical power supply, such as a battery, and a control switch. In one embodiment, the handle also includes a pathway 31 for delivering or removing substances from the oral cavity. For example, pathway 31 can provide for the entrance and/or egress of air, the delivery of treatment agents and/or drugs, and water evacuation.

Figure 4:
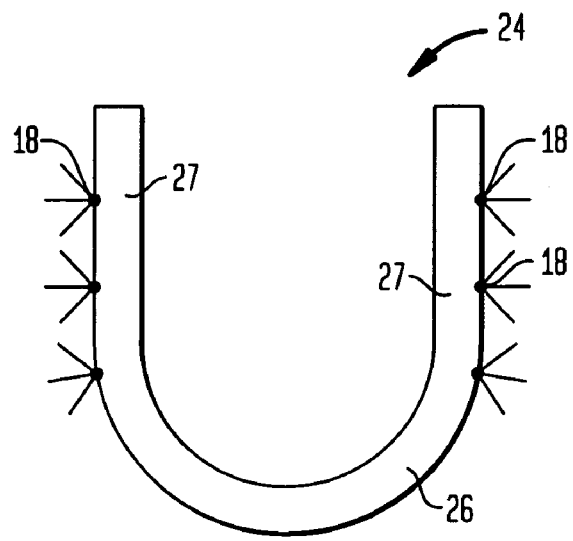
FIG. 4 illustrates another embodiment of the light emitting mouthpiece of the present invention.

FIG. 4 shows another embodiment of light emitting mouthpiece 24 including two substantially parallel prongs 27 defining a generally "U" shaped body portion. Each prong preferably has at least one optical radiation source 18, and preferably multiple optical radiation sources, which are positioned for radiating cheek and facial tissue when the body is positioned within a user's oral cavity. Various other shapes are also useful including, for example, mouthpieces that surround both sides of the user's teeth in a manner similar to an athletic mouthguard. Optical radiation sources can be disposed on the inside of such mouthpieces to provide phototherapeutic radiation to the teeth and gums or disposed toward the outside to deliver phototherapy to the cheeks or facial tissue.

The optical radiation source disposed in the light-emitting oral appliances of the present invention can preferably include a variety of radiation sources capable of delivering electromagnetic radiation in the range of about 280 nm–100000 nm with power densities in the range of about 1–50,000 mW/cm$^2$ and total power 1 mW–10W. One preferred radiation source is a LED or LED-matrix irradiator emitting at 1 to 20 different wavelengths. Radiation sources for the oral appliance are preferably compact, effective, low cost and provide the necessary wavelengths and power. In a preferred embodiment, the output spectrum of such radiation sources should preferably be in the range of about 280–12000 nm and have a power in the range of about 10 mW to 1 W. The terms "light" and "radiation" are used interchangeably throughout this application to encompass the entire spectral range of optical radiation useful in the phototherapy, for example, a range of about 280 nm to about 100,000 nm, and are not limited to the visible spectrum. The size of the radiation source should preferably be small enough to package in an oral appliance and be sufficiently efficient to be powered by a battery for at least 1–15 minutes.

In one embodiment, the light radiation source is solid-state lighting (SSL) including a light emitting diode (LED) and LED variations, such as, edge emitting LED (EELED), surface emitting LED (SELED) or high brightness LED (HBLED). The LED can be based on different materials such as AlInGaN/AlN (emitting from 285 nm), SiC, AlInGaN, GaAs, AlGaAs, GaN, InGaN, AlGaN, AlInGaN, BaN, InBaN, AlGaInP (emitting in NIR and IR), etc. LEDs also include organic LEDs which are constructed with a polymer as the active material and which have a broad spectrum of emission. The radiation source can be an LED such as shaping of LED dies, LED with transparent confinement region, photonics crystal structure, or resonant-cavity light-emitting diodes (RCLED).

Other possibilities include a superluminescent diode (SLD) or LED which preferably can provide a broad emission spectrum source. In addition, laser diode (LD), waveguide laser diode (WGLD), and a vertical cavity surface emitting laser (VCSEL) can also be utilized. The same materials used for LED's can be used for diode lasers. Other possibilities include a fiber laser (FL) with laser diode pumping. Fluorescence solid-state light source (FLS) with electro or light pumping from LD, LED or current/voltage sources can also be the radiation source. The FLS can be an organic fiber with electrical pumping.

Lamps such as incandescent lamps, fluorescent lamps, micro halide lamps or other suitable lamps may also be used with the present invention. A lamp can provide the radiation source for white, red, NIR and IR irradiation. For the 5–100 micron range, quantum cascade lasers (QCL) or far infrared emitting diodes can be used. One skilled in the art will appreciate that a variety of radiation sources can provide the necessary optical radiation for the optical appliance depending on size, power requirements, desired treatment regimen, and combinations thereof.

An LED, a laser diode, or a microlamp can generate heat energy that is up to 20 times higher than the generated optical energy. To accommodate unwanted waste heat, the light emitting oral appliance can include heat transfer and/or cooling mechanisms. For example, head portion 12 of the exemplary light emitting toothbrush can be at least partially formed of a heat conducting material for dissipating heat generated by the radiation source. For example, with reference to FIG. 2B, the head portion 12 can include a head frame 38 that is constructed from a material having high thermal conductivity and/or good heat capacitance and is thermally coupled to the radiation source 18 to extract heat therefrom. This frame can be extended to external surfaces of the head, which can contact saliva or tissue during the use of the toothbrush. One skilled in the art will appreciate that a variety of materials can provide the necessary heat transfer such as, for example, metals including aluminum, copper or their alloy, ceramic and composite materials such as plastics having high thermally conductive components, such as carbon fiber. In one embodiment, heat is removed by heat transfer from the frame to adjacent tissue and/or saliva in contact with the light emitting toothbrush or light emitting mouthpiece. This heat can be employed for gentle heating of the oral tissue, and/or a paste applied to a portion of oral tissue, to provide additional or enhanced therapeutic effects.

Figure 5:
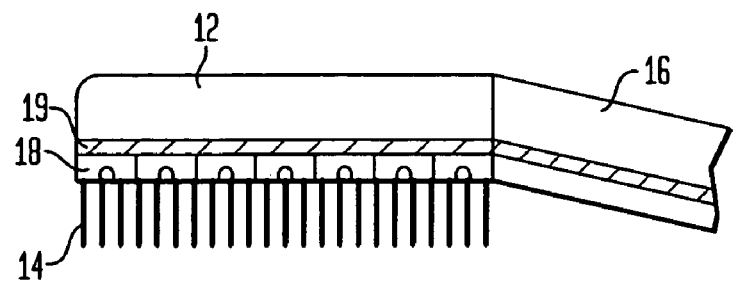
FIG. 5 illustrates another embodiment of the light emitting toothbrush of the present invention.

In another aspect of the invention, heat can be transferred along the head portion of the light emitting toothbrush to the handle portion and dissipated into the surrounding environment, e.g., an operator's hand. FIG. 5 schematically illustrates a light emitting toothbrush according to one embodiment of the invention having a head portion 12, a handle portion 16, and at least one radiation source 18 incorporated in the head portion. A heat transfer element 19, e.g., in the form of an elongated element, e.g., a heat pipe, constructed of a material having high thermal conductivity, is thermally coupled at one end to the radiation source and at another end to a portion of the handle so as to transfer heat generated by the source to the handle. The portion of the handle to which the heat transfer element is coupled can have optionally a corrugated surface to facilitate heat transfer to the ambient environment, e.g., a user's hand.

Figure 6:
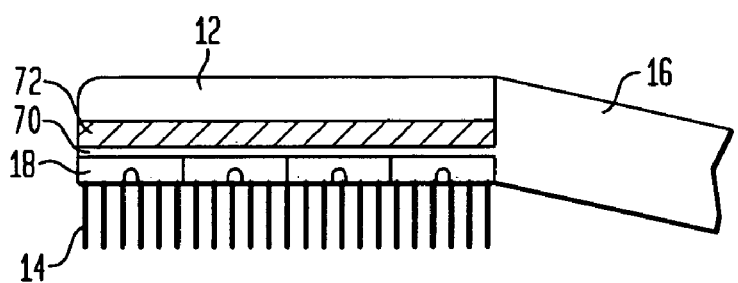
FIG. 6 illustrates another embodiment of the light emitting toothbrush having a heat transfer element.

With reference to FIG. 6, in another embodiment, a phototherapeutic oral appliance according to the teachings of the invention can include a heat transfer element 70 that transfers heat generated by a radiation source to a reservoir 72 in which a phase transfer material can be stored. The phase transfer material, for example, ice, wax, or other suitable materials, absorbs the heat to change its phase, for example, from liquid to gas or solid to liquid, thereby dissipating the heat. Preferably, the phase transfer material has a melting or evaporation temperature in the range of about 30 to 50° C.

Although the above discussed examples of heat transfer elements are made with reference to the light emitting toothbrush, one skilled in the art will appreciate that the heat transfer elements can be used in any of the oral appliances of the present invention. In particular, these heat transfer elements can provide for the storage or transfer of heat from the radiation source in the light emitting mouthpiece to adjacent tissue, a handle, and/or the surrounding environment.

Figure 7:
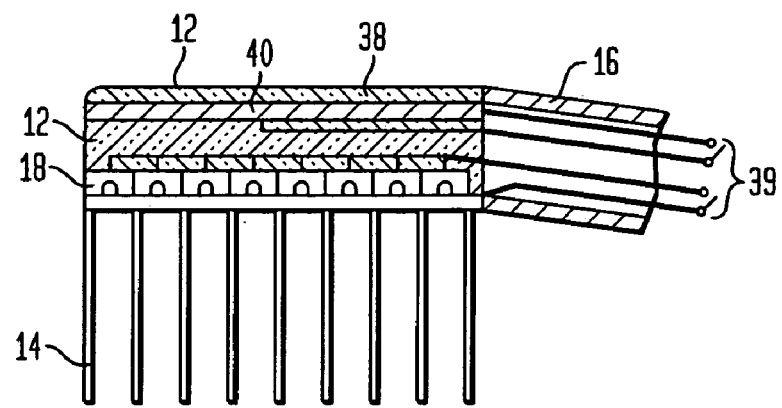
FIG. 7 illustrates another embodiment of the light emitting toothbrush having a heater.
Figure 8:
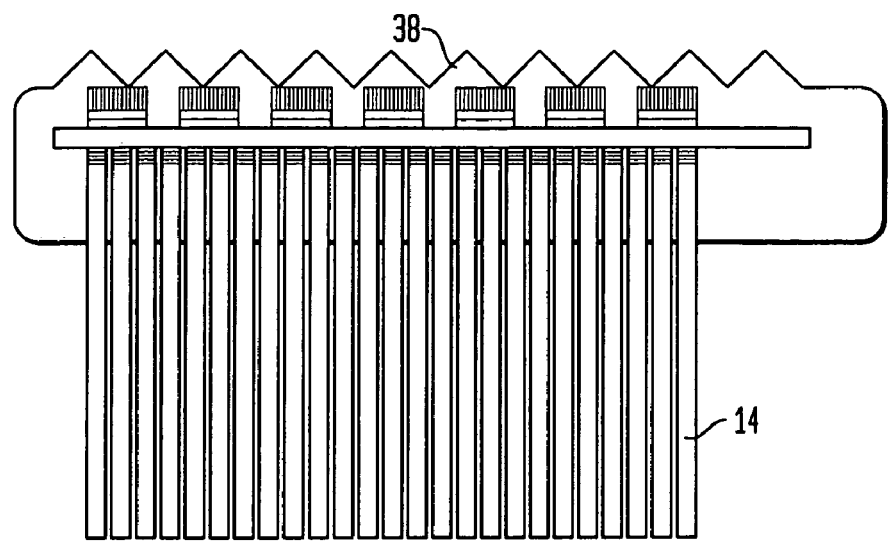
FIG. 8 illustrates another embodiment of the light emitting toothbrush having a head frame shaped for heat transfer.

In some embodiments, the light emitting oral appliance can include a heater for heating a target portion of the oral cavity, for example, while therapeutic radiation is applied to the target portion. Thermal therapy is useful in some treatment regimens and provides an additive or symbiotic effect when combined with phototherapy. FIG. 7 shows electric heater 40 positioned within head portion 12 of a light-emitting toothbrush according to one embodiment of the invention. To facilitate heat transfer from the heater to adjacent tissue, head frame 38 can have a corrugated shape as shown in FIG. 8.

In some embodiments, heating is provided by a radiation source. In one aspect of the invention, the heater 40 is a radiation source that is distinct from the radiation source generating therapeutic radiation, e.g., radiation source 18. In another aspect, heating can be provided by the same radiation source utilized for providing therapeutic radiation. For example, in such an embodiment, the radiation source can generate broadband radiation, or radiation in two or more bandwidths, such that at least one bandwidth is suitable for heating the oral cavity tissue. Alternatively, multiple radiation sources can be used, at least one of which provides radiation in a suitable wavelength range for deep heating of tissue. Exemplary deep heating radiation includes radiation having a wavelength in the range of about 0.38 to about 0.6 microns or a range of about 0.8 to 100 microns. One skilled in the art will appreciate that a variety of electric and non-electric heaters can be used with the oral appliances of the present invention.

Figure 9:
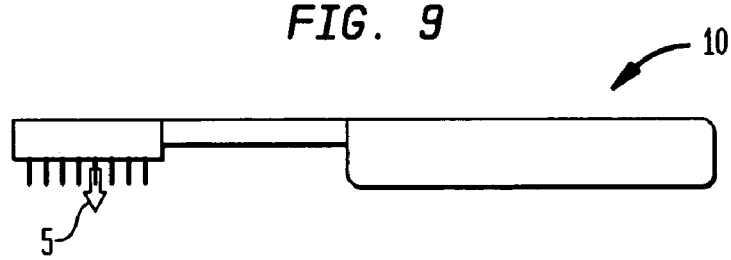
FIG. 9 illustrates another embodiment of the light emitting toothbrush directing radiation is a single direction.
Figure 10:
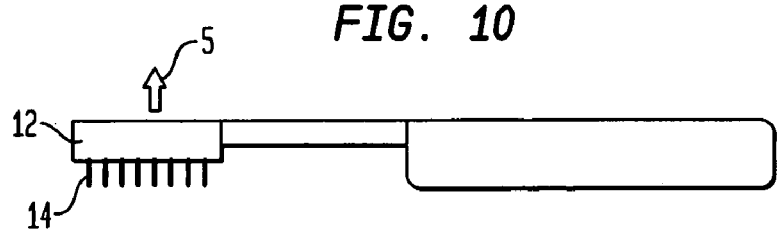
FIG. 10 illustrates the light emitting toothbrush of FIG. 9 directing radiation in a different direction.
Figure 11:
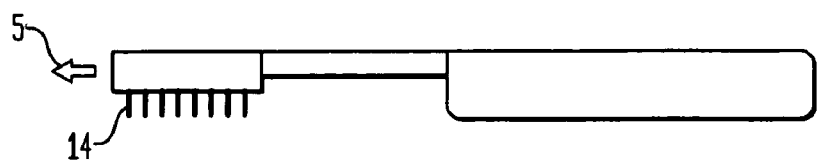
FIG. 11 illustrates the light emitting toothbrush of FIG. 9 directing radiation in a different direction.

Depending on the desired treatment regimen, the optical radiation delivered from the oral appliance of the present invention can be selectively directed to different regions of the oral cavity. FIGS. 9–16 illustrate various embodiments of a light emitting toothbrush according to the teachings of the invention for selectively treating different tissue areas. FIG. 9 illustrates a unidirectional embodiment in which the optical radiation generated by a radiation source is directed substantially in the same area as a plurality of bristles which are touching tissue, e.g., through the bristles themselves. In use, the radiation will be directed primarily toward hard tissue, e.g., a user's teeth. Alternatively, FIG. 10 shows an embodiment where the optical radiation is directed away from the direction of the bristles to illuminate primarily soft tissue, such as facial tissue, e.g., tissue within the cheek. FIG. 11 illustrates another embodiment of a light-emitting toothbrush according to the invention having a light source for directing optical energy radiating from the front of the device, e.g., in a direction substantially perpendicular to the bristles, into selected portions of a user's optical cavity. This embodiment is particularly suited for selectively irradiating the soft tissue of a user's throat region.

Figure 11A:
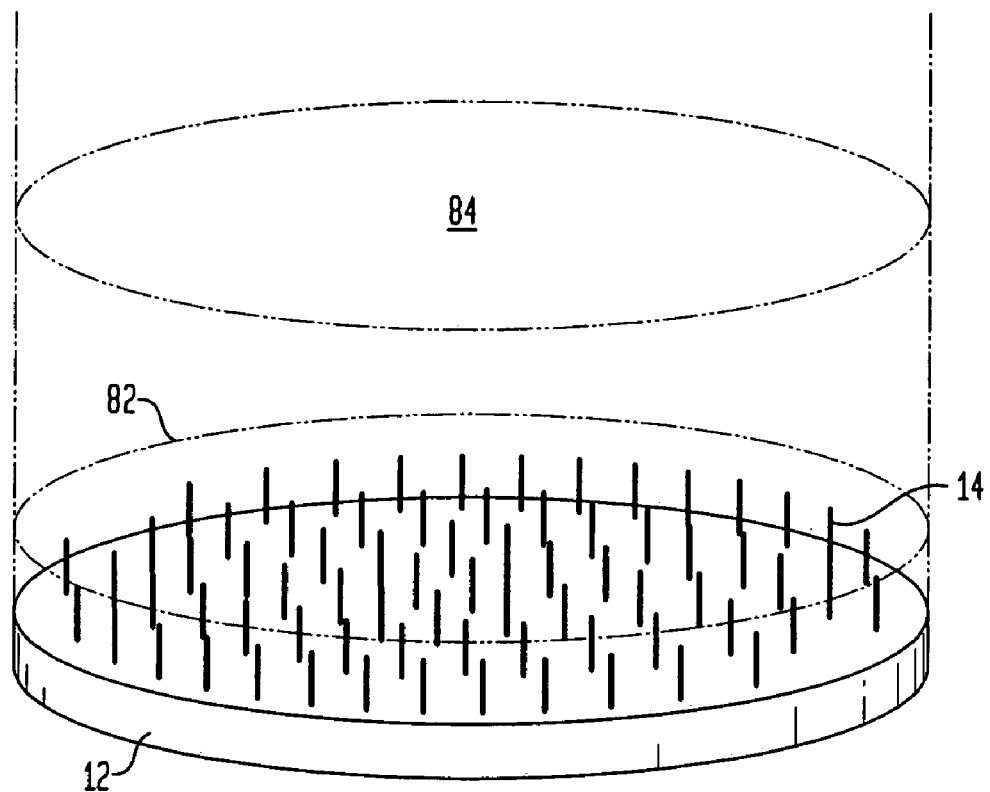
FIG. 11A illustrates another embodiment of the light emitting toothbrush of the present invention.

In one aspect of the invention, at least a portion of the radiation is emitted in a direction other than towards the hard tissue of teeth. This can be accomplished with the light emitting toothbrush of the present invention by emitting radiation in a direction other than that represented by the cross sectional area defined by a circumference which surrounds the bristles or extensions thereof. FIG. 11A illustrates head portion 12 of a light emitting toothbrush with bristles 14. As shown, the circumference of the bristles defines an area 82 which can be extended outward from the bristles to create column 84. Preferably, optical radiation emitted by the light emitting toothbrush to treat primarily soft tissue does not intersect column 84.

Figure 12:
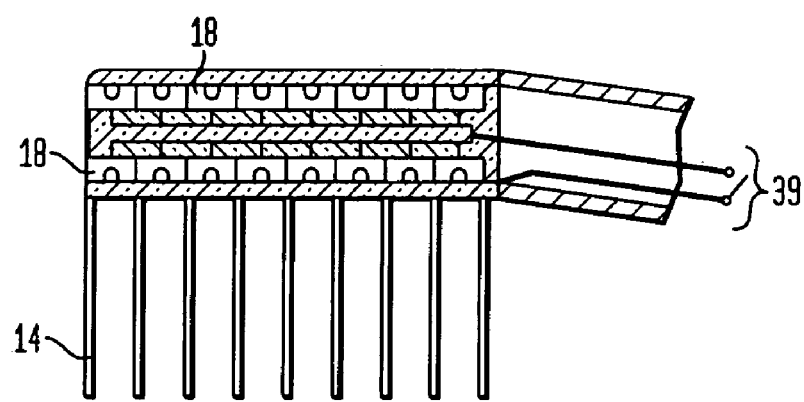
FIG. 12 illustrates a light emitting toothbrush of the present invention capable of directing radiation in more than one direction.
Figure 13:
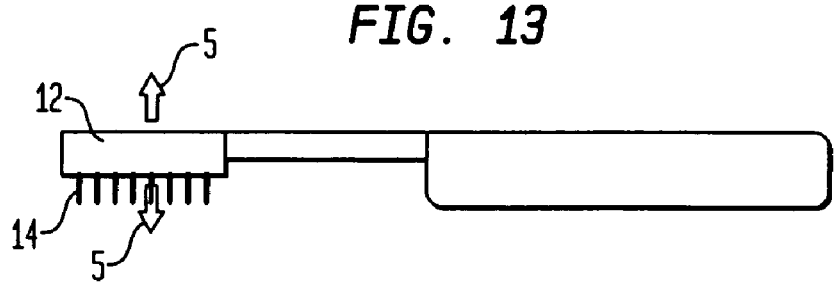
FIG. 13 illustrates a light emitting toothbrush of the present invention directing radiation in multiple directions.

In another embodiment, optical radiation can be directed in multiple directions from the same oral appliance (as shown by directional arrows 5 in the various FIGS). For example, a light-emitting toothbrush of the invention can include two groups of LEDs, as shown in FIG. 12, such that one group can radiate in a direction substantially parallel to the bristles, while the other group can radiate in the opposite direction. FIG. 13 illustrates the direction of the radiation leaving the device of FIG. 12.

Figure 14:
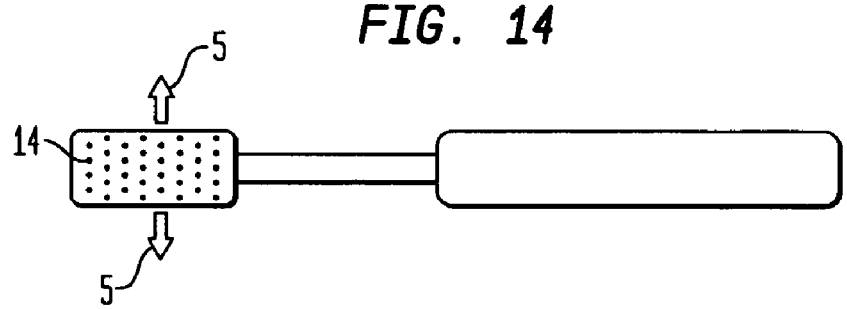
FIG. 14 illustrates another embodiment of the light emitting toothbrush of FIG. 13.
Figure 15:
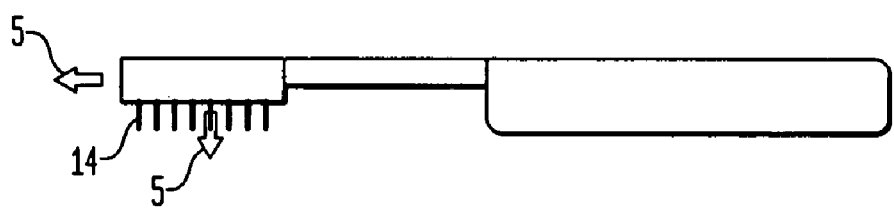
FIG. 15 illustrates another embodiment of the light emitting toothbrush of FIG. 13.
Figure 16:
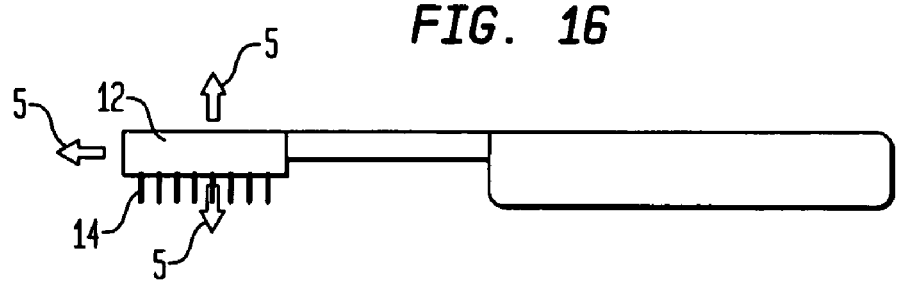
FIG. 16 illustrates another embodiment of the light emitting toothbrush of FIG. 13.
Figure 17:
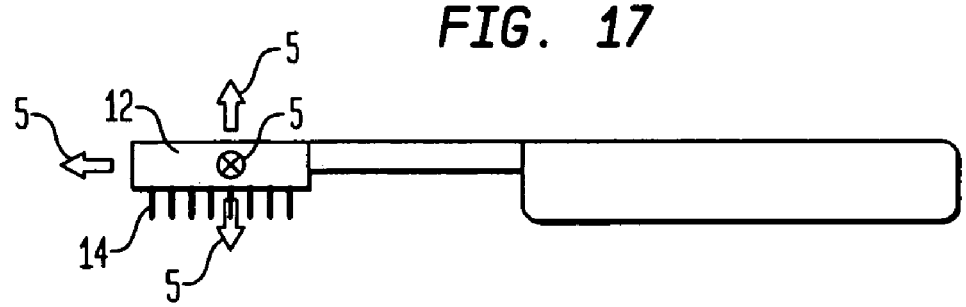
FIG. 17 illustrates another embodiment of the light emitting toothbrush of FIG. 13.

FIG. 14 shows another multidirectional light emitting toothbrush with radiation leaving from either side of the device (bristles coming out of the page). FIG. 15 shows radiation directed toward the front and in the direction of the bristles. Finally, FIGS. 16 and 17 illustrate other aspects of the multidirectional light emitting toothbrush having radiation directed in more than two directions. FIG. 16 illustrates a three directional embodiment, while FIG. 17 shows a five directional light emitting toothbrush (front, both sides, top and bottom).

Figure 18:
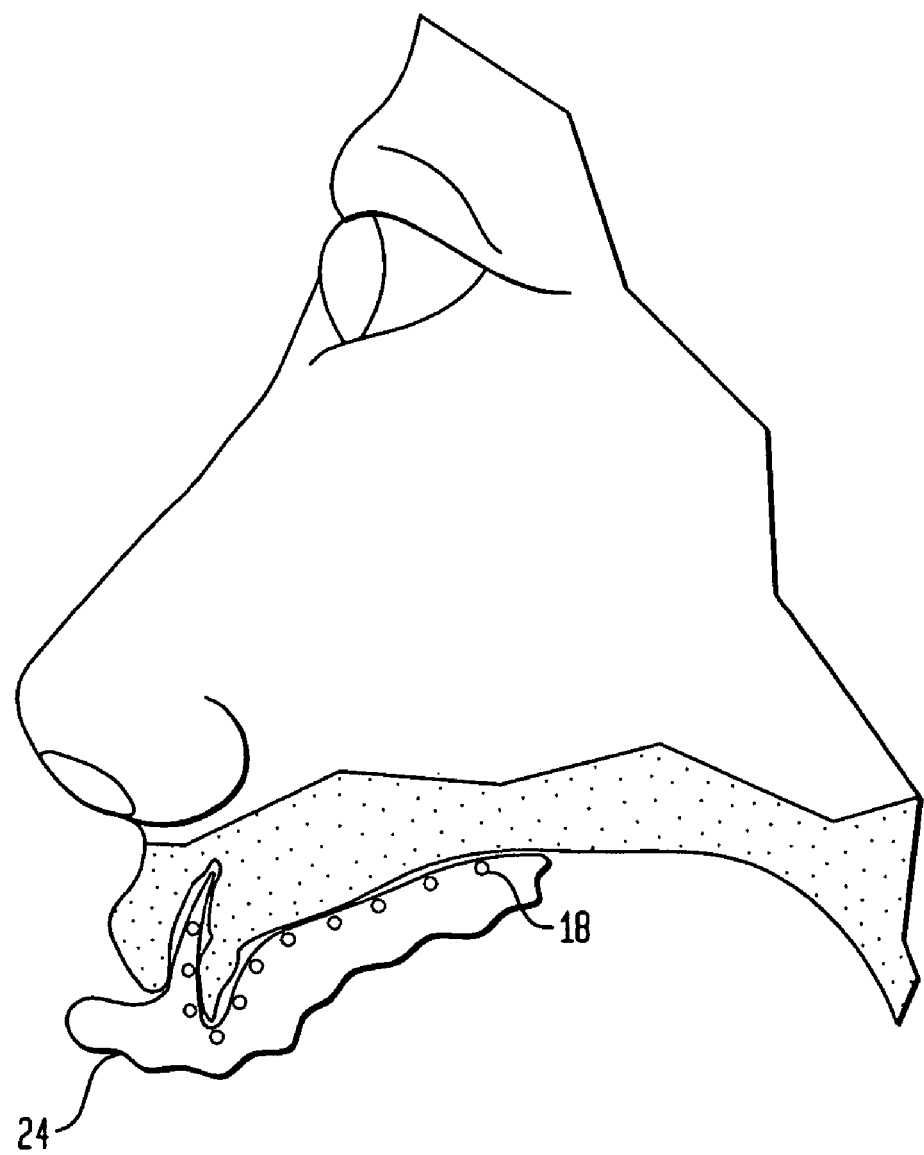
FIG. 18 illustrates another embodiment of the light emitting mouthpiece of the present invention capable of directing radiation at the tongue.
Figure 19:
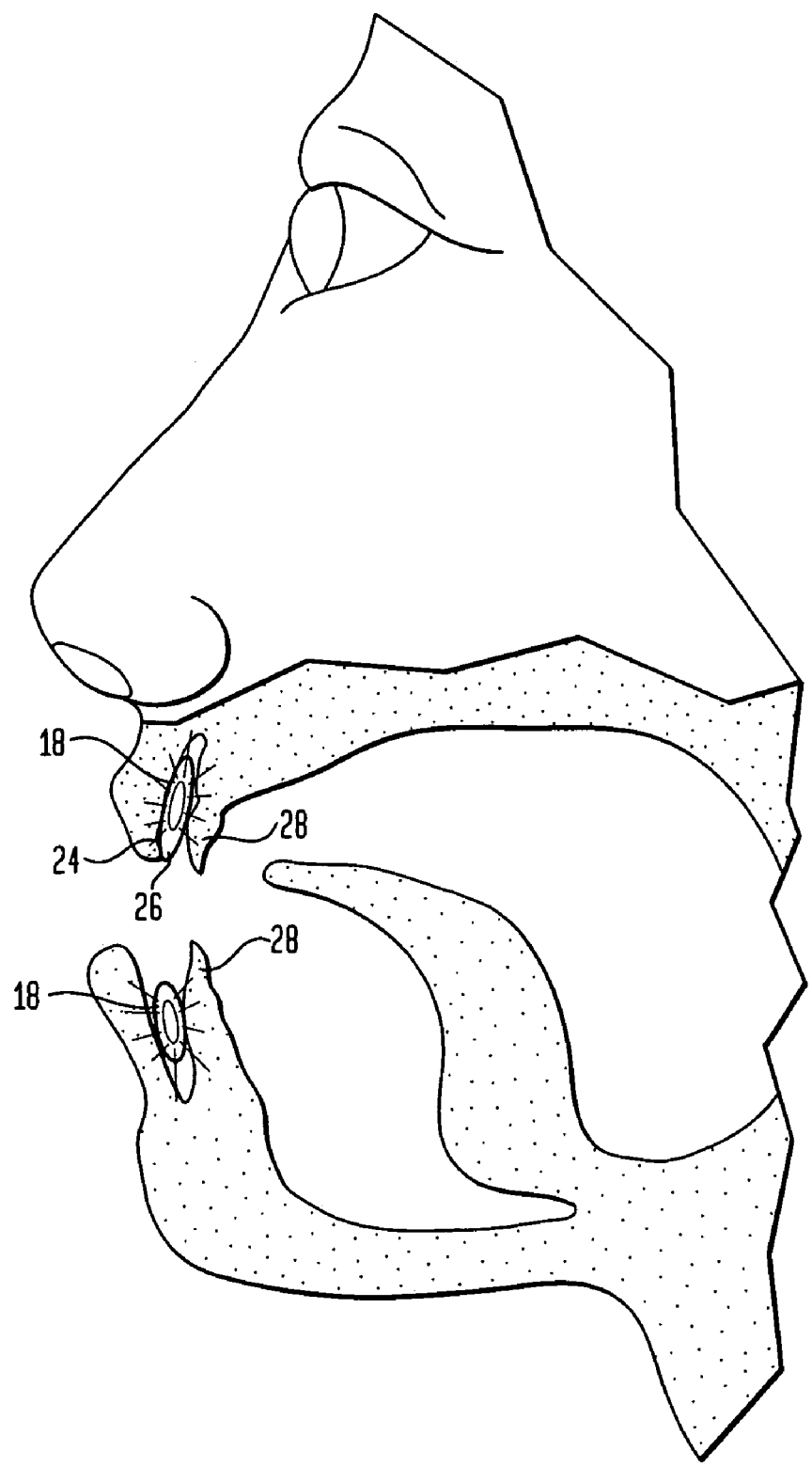
FIG. 19 illustrates another embodiment of the light emitting mouthpiece of the present invention capable of being positioned between the teeth and cheek.
Figure 20:
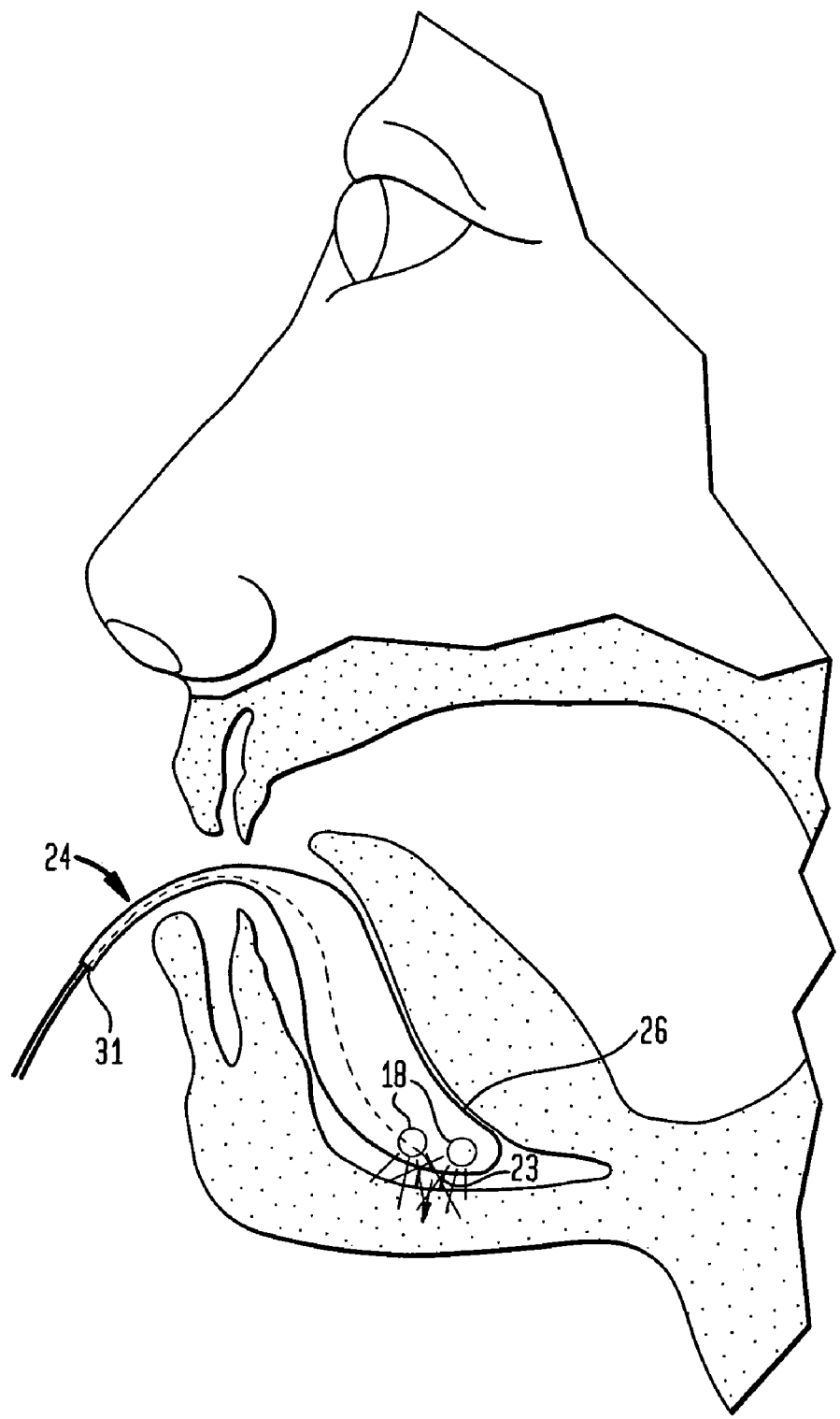
FIG. 20 illustrates another embodiment of the light emitting mouthpiece of the present invention capable of delivering radiation to the floor of the oral cavity.

The illustrated examples of multidirectional light emitting oral appliances similarly applies to the light emitting mouthpiece of the present invention. As shown in FIGS. 3 and 4, optical radiation can be directed from body portion 26 of light emitting mouthpiece 24 toward various structures or tissue types within or surrounding the oral cavity. FIG. 18 shows a light emitting mouthpiece designed to direct radiation around the tongue. This embodiment is useful for treating diseases of the tongue, such as excessive bacterial growth. In another embodiment, light emitting mouthpiece 24 can be designed to treat tooth, gum, and/or cheek tissue. For example, FIG. 19 shows body portion 26 positioned between the teeth and cheek tissue. In this embodiment, optical energy is selectively directed toward cheek (wall of the oral cavity), gum, and tooth tissue. In yet a further embodiment, optical radiation from the light emitting mouthpiece can be directed toward the soft tissue beneath the tongue as shown in FIG. 20, or other parts of oral cavity to support, e.g., oral drug or vitamin delivery. A drug or vitamin 23 can be delivered to mucosa through opening 31, for example, in liquid form while the light source 18 directs radiation on the drug and mucosa. This radiation can be selected to increase permeability of the mucosa for enhanced uptake and penetration of the drug into the oral cavity tissue. Alternatively, or in addition, the radiation can activate the drug for better therapeutic effect. Such a method of drug delivery can be employed at a physician's office or at home.

Figure 20A:
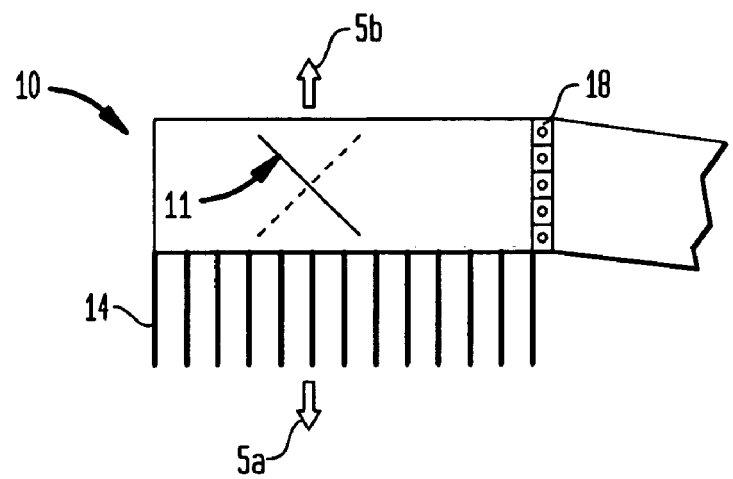
FIG. 20A illustrates a light emitting toothbrush of the present invention with an optical element.

The direction in which the optical radiation is emitted can be controlled in a variety of ways. In one embodiment, optical radiation source 18 can be disposed such that the radiation it produces travels toward the target tissue. This can be accomplished by positioning the optical radiation source at or near the surface of the oral appliance and placing the surface adjacent to the target tissue. In another embodiment, an optical element, e.g., a reflective or a refractive element, can be coupled to the radiation source for selectively directing radiation emitted by the source. The optical element can include, for example, rotatable mirrors, prisms, and/or diffusers, which direct the optical radiation toward target tissue. For example, with reference to FIG. 20A, a light-emitting toothbrush 10 according to the one embodiment of the invention can include a radiation source 18 optically coupled to a rotatable mirror 11 that can direct radiation emitted by the source 18 either along a plurality of bristles 14, as indicated by an arrow 5a, or in a direction substantially opposite to the bristles, as indicated by an arrow 5b.

In addition to providing single or multidirectional optical radiation, the oral appliance of the present invention can supply single or multiple bands of optical radiation. For example, some treatment regimens may call for a single wavelength band such as a single blue color (central wavelength of 400–430 nm), a single green color (central wavelength of 540–560 nm), a single red color (central wavelength 620–635, 660), or a NIR single color (central wavelength 800–810 nm). Alternatively, a combination of these or other distinct wavelength bands could be applied, including two, three, or more distinct bands of optical radiation. For example, two separate wavelength bands can be employed to treat the same conditions more effectively or to treat two different conditions.

Multiple distinct wavelength bands can be achieved in a variety of ways. In one aspect of the invention, a broad band radiation source is used with an optical element to filter out unwanted wavelengths. For example, a filter or filters can remove all wavelengths from a broad spectrum with the exception of those in the blue and red portions of the spectrum. In another aspect of the invention, multiple distinct bands can be achieved with multiple radiation sources, each source providing optical radiation in a desired band. And in yet another aspect, a single radiation source which produces multiple distinct bands can be used. As an example, a single LED can be used to produce two or more distinct wavelength bands. Fluorescence conversion of radiation energy can be employed for generating additional wavelengths. As another example, a diode pumped fiber laser can be used to generate two wavelengths, one corresponding to the diode laser pumping the fiber and the other corresponding to the fiber laser wavelength.

In some embodiments of the oral appliance, it may be desirable to change wavelength bands. This can be accomplished with the light emitting toothbrush of the present invention by using removable head portions. Each head portion can include a radiation source producing a light of a different wavelength. A user can then choose the desired wavelength band by selecting among removable head portions. Alternatively, the handle portion can include a broad band light source and the removable head portions can include filters to isolate desired wavelength bands.

Figure 21:
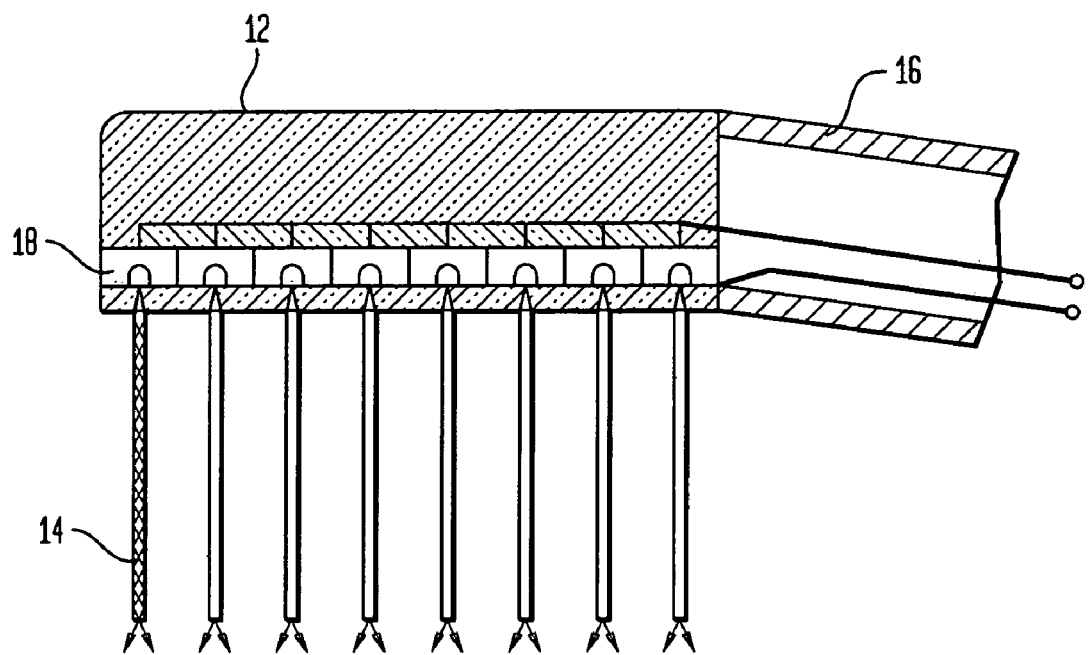
FIG. 21 illustrates a light emitting toothbrush of the present invention with an active optical bristle.

As described above, various embodiments of the light-emitting toothbrush of the invention include bristles for performing functions that include, but are not limited to, mechanical cleaning of hard and soft tissue, massage, blood circulation activation, compression of soft tissue for improved light penetration, and improved light delivery. For example, FIG. 21, which is a cut-away side view of head portion 12 of a light emitting toothbrush of the invention, shows a plurality of bristles 14 coupled to head portion 12 that are preferably constructed of a material substantially transparent to radiation within at least one of the bandwidths produced by radiation source 18. In addition, bristles 14 can preferably help direct optical energy and/or facilitate transfer of the optical radiation to tissue, preferably with minimal loss. Providing minimal loss in coupling energy generated by radiation sources into the oral cavity tissue advantageously enhances utilization efficiency of the radiation sources and minimizes costs associated with operating the light emitting toothbrushes and mouthpieces of the invention.

Figure 22:
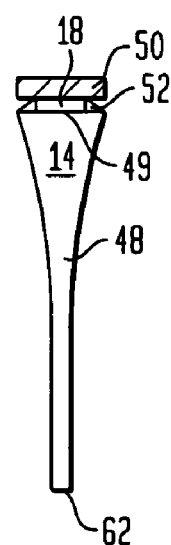
FIG. 22 illustrates an active optical bristle of the present invention.

FIG. 22 shows a bristle, herein also referred to as 'active bristle', having an elongate body 48 formed of a transparent material, which is mated at a proximal end 49 with the radiation source 18, such as LED or diode laser, substrate 50, and optical reflective elements 52. The direct optical coupling of the bristle with the radiation source 18, for example, via an optical glue or other suitable mechanism, advantageously enhances coupling of radiation into the bristle, which can in turn function as a waveguide for transferring the radiation to its distal end 62 for delivery to the user's oral cavity. The reflective optical elements 52, for example, mirrors, direct light emitted in directions other than that of the bristle into the bristle, thereby enhancing optical coupling of the bristle to the light source. For example, the reflective element 52 can be used for coupling edge emitting radiation from LED into the bristle. In one embodiment, substrate 50 and optical elements 52 direct optical energy by way of their highly reflective surface. This design advantageously maximizes extraction of light from LED and its delivery to oral cavity tissue.

In one embodiment, each bristle can be optically coupled to radiation source 18, and in a further embodiment, each bristle can be coupled to an individual LED. For example, each bristle can be in substantial register with a single radiation source 18 (FIG. 22). To facilitate such mating, bristle 14 can be shaped at its proximal end 49 for receiving an emitting surface of the radiation source 18.

Figure 23:
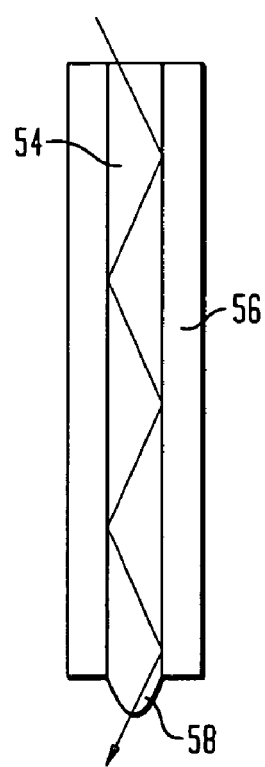
FIG. 23 illustrates another embodiment of the active optical bristle of the present invention.

In some embodiments, bristle 14 acts as a waveguide for directing radiation from a radiation source to a portion of a user's oral cavity. For example, FIG. 23 schematically illustrates a bristle having a highly refractive core 54 and a low refractive cladding 56. Optical radiation is directed through the core 54 and is contained by the cladding 56. When the optical energy reaches the open bristle tip 58, the radiation is released. This embodiment allows radiation to be directed to tissue in contact with bristle tip 58. To further assist with transfer of the optical radiation to tissue, the refractive index of the bristle tip and target tissue can be matched. For example, because of the difference between the refractive index of air and the bristle, the bristle 14 can mostly contain the optical radiation by internal reflection. Only when the bristle touches tissue, is there an increase in the amount of optical radiation released.

Figure 24:
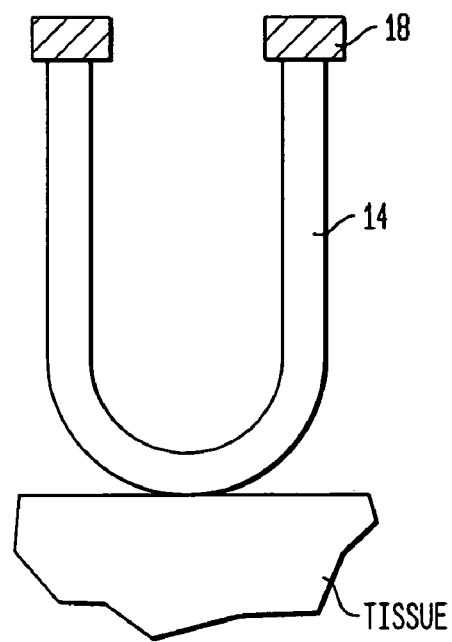
FIG. 24 illustrates yet another embodiment of the active optical bristle of the present invention.

In some embodiments of the invention, the bristles are shaped so as to allow controlled leakage of radiation at selected points. For example, FIG. 24 illustrates another embodiment of bristle 14 in the form of an optical loop. Both ends of the loop are connected to an optical radiation source 18. Light is generally contained within the loop except for at the bend where the disturbed complete or almost complete internal reflection effect allows light leakage. The bend can be positioned in a target tissue area to deliver optical radiation. Such bristles also enhance eye safety characteristics of the device because they can ensure that light is emitted only at selection portions, e.g., portions in contact with oral cavity tissue. Such an active bristle, which allows extraction of light through complete internal reflection into tissue in contact therewith, can be particularly useful for high power light emitting tooth brushes when eye safety in of special concern. A light emitting toothbrush of the invention can hence include a bundle of bristles formed of active bristles described above.

Figure 25:
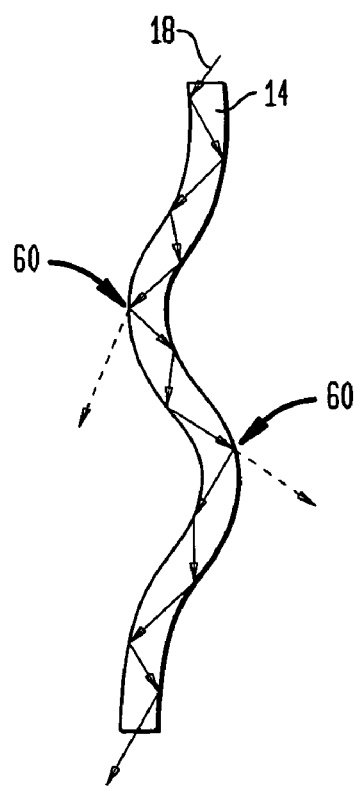
FIG. 25 illustrates yet another embodiment of the active optical bristle of the present invention.
Figure 26:
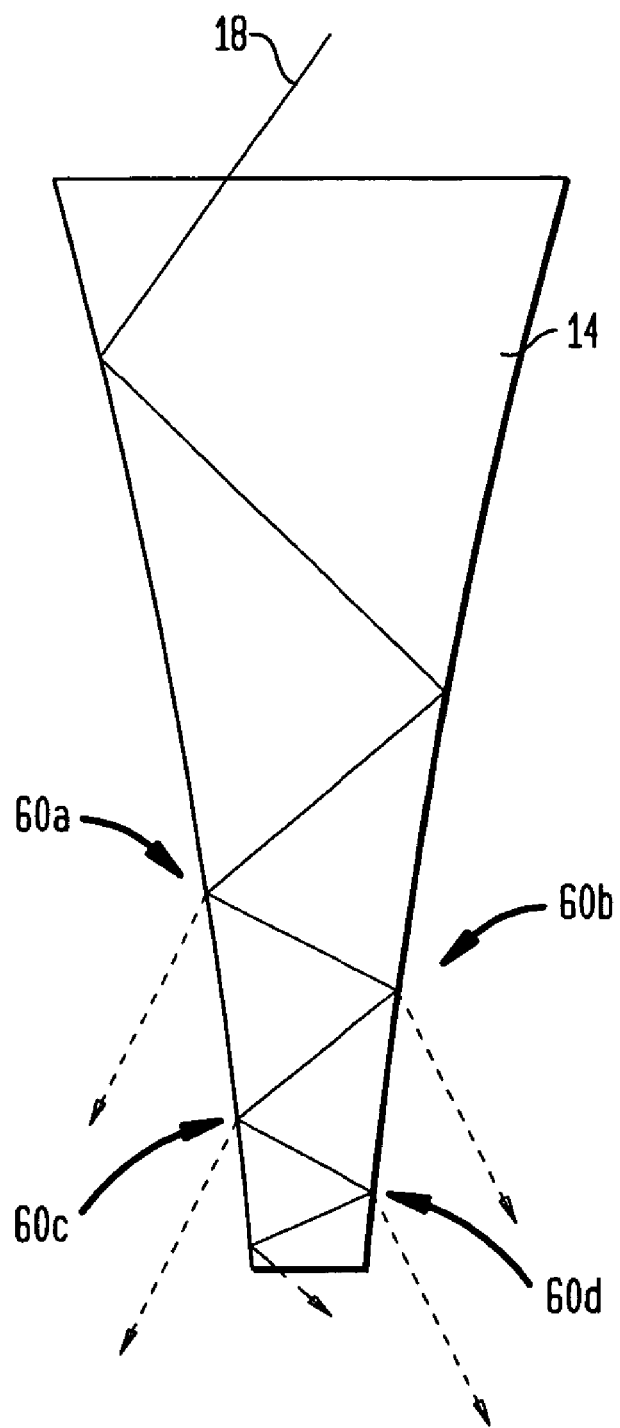
FIG. 26 illustrates yet another embodiment of the active optical bristle of the present invention.

The bristle can have other shapes which facilitate controlled leakage of optical radiation. FIG. 25 shows a spiral bristle which allows light leakage 60 at the points with maximum curvature. FIG. 26 illustrates a conical type bristle extending from a base to a smaller tip 62 with a controlled tip angle. As a radiation ray traverses the bristle from the base towards the tip, its angle of incidence at the interface of the bristle and the surrounding environment increases such that at certain points, such as points 60*a*, 60*b*, 60*c*, and 60*d*, radiation leaks out of the bristle.

In another embodiment, it may be desirable to release the optical energy in a dispersed pattern and reduce the formation of hot spots by doping the bristles, or improving emission spectra of the radiation sources. For example, the bristles can include a fluorescent material dispersed therein, which will fluoresce when exposed to optical radiation. Alternatively, a lasing material can be used to dope the bristles, such as a dye.

The body of the light emitting mouthpiece of the present invention can also be designed to so as to allow controlled leakage or dispersal of radiation based on the concepts described with respect to the bristle. For example, light can be contained within mouthpiece body 26 except for at select points and/or the body can include light dispersing material.

Figure 27A:
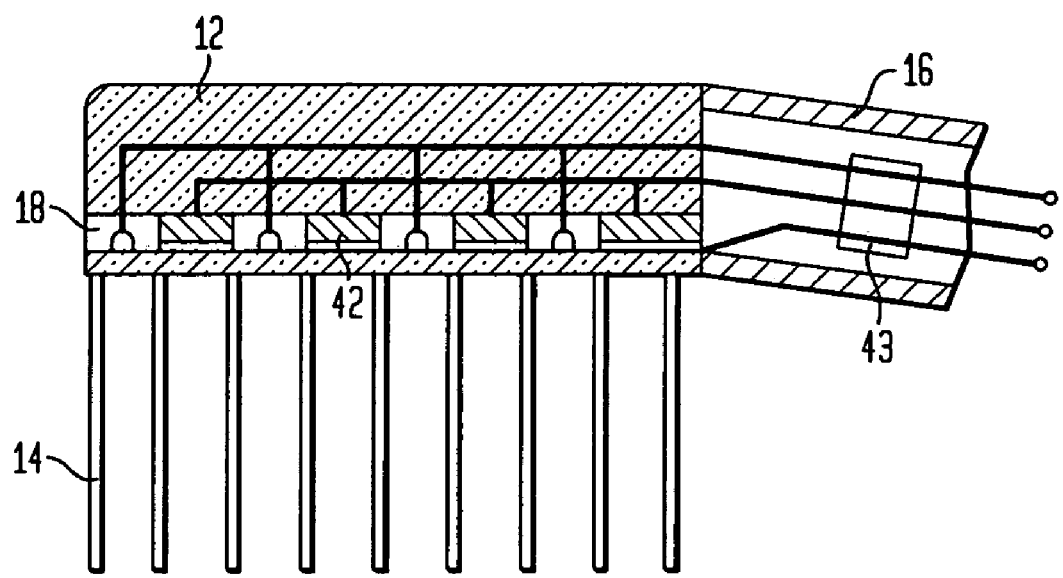
FIG. 27A illustrates another embodiment of the light emitting toothbrush of the present invention having a sensor and a controller.
Figure 27B:
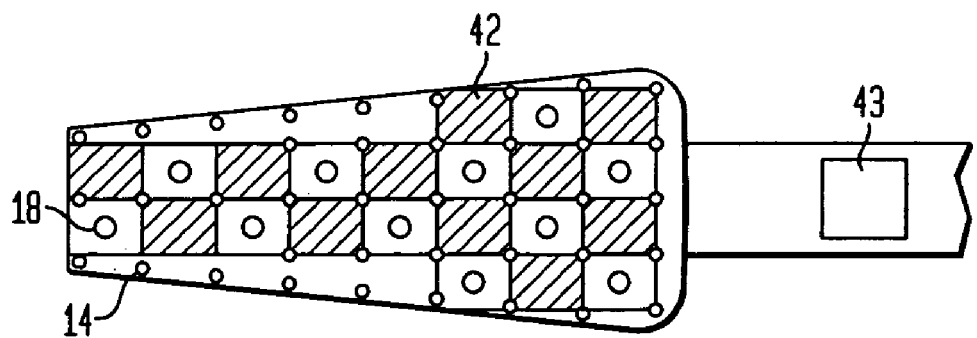
FIG. 27B is another view of the light emitting toothbrush of FIG. 27A.

An oral appliance of the present invention can additionally include sensors for monitoring treatment and/or diagnosing conditions within the oral cavity. FIGS. 27A and 27B show a cut-away side view and a bottom view, respectively, of a head of a diagnostic light emitting toothbrush containing one or more fluorescence detection modules 42. Each module preferably contains an optical filter and a photosensitive microchip which can be connected to an electronic detection system. The fluorescence signal detected by the detection modules can provide information about the concentration of bacteria in a periodontal packet, hard tissue (carious lesion), saliva or mycosis, as well as, information about teeth whitening and brightening. An additional fluorescence signal can be employed for early diagnostic of different mucosal diseases including cancer. In one embodiment, the oral appliance can include a signal mechanism for indicating to a user when a treatment is complete or a condition has been detected based on the fluorescence signal. In another embodiment, a reflectometer can be incorporated in a LETB or LEMP of the invention. For example, photo-induced current through LED can be utilized for reflected light detection. In other embodiments, separate LED and photodetectors can be employed for measuring reflections at different wavelengths. Reflections can be employed for diagnostic of caries, whitening, brightening of hard tissue and/or mucosa diseases. In other embodiments, the light from LETB or LEMP can be employed for translucence diagnostic of caries of front teeth. Wavelengths in a range of about 450 to about 800 nm can be used for this purpose.

Sensors can also provide the user with a variety of other information, such as, sensing and alerting a user when a treatment session is complete, when the oral appliance is properly positioned, when the oral appliance is in contact with tissue, and/or if the temperature in the treatment area rises above a predetermined level. Sensors can also be used with a controller to provide autofeedback control of a treatment session(s). In one exemplary embodiment, a controller is coupled with a diagnostic sensor to control the radiation source based on signals from the sensor. In another optional embodiment, a controller could be combined with a sensor to emit radiation only when the oral appliance is in contact with tissue.

FIGS. 27A and 27B illustrate controller 43 disposed in the light emitting toothbrush of the present invention. A person skilled in the art will appreciate that a variety of controllers such as, for example, microswitches, microprocessor, and other analog or digital devices can be used to regulate the various features and treatment parameters of the light emitting oral appliance.

Figure 28:
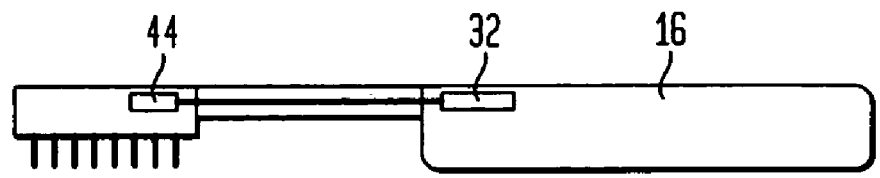
FIG. 28 illustrates another embodiment of the light emitting toothbrush of the present invention having a vibrating mechanism.
Figure 29:
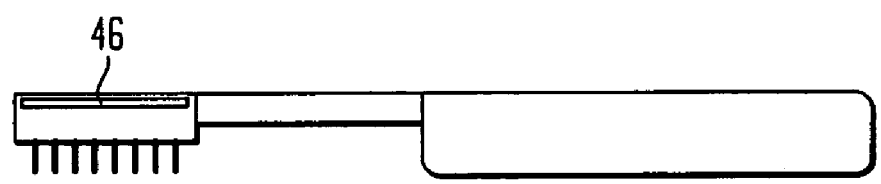
FIG. 29 illustrates another embodiment of the light emitting toothbrush of the present invention.

In another embodiment, the oral appliance of the present invention can include various features to assist with treatment. For example, the light emitting toothbrush or light emitting mouthpiece can include vibrating mechanisms, such as mechanical or ultrasonic vibrators, to assist with mechanical cleaning. FIG. 28 illustrates a light emitting toothbrush with a mechanical vibrator 44. The vibrations generated by the vibrator can be employed not only for better tooth cleaning but also for enhancing phototherapy. For example, the vibrations can increase light penetration into soft tissue and/or increase the effect of light treatment on cells and/or bacteria. One mechanism of such enhancements is better oxygen delivery to a phototreated target. FIG. 29 shows a light emitting toothbrush with an additional component 46 for creating an electrical field, magnetic field, chemical realize, and/or low level non stable isotope radiation. Component 46 can be an electrically charged element, magnet, chemical container, isotope container etc.

In yet another embodiment, the present invention can include reflective surfaces to more efficiently deliver radiation to tissue. When radiation is delivered to a target area, some of the radiation can be reflected by the tissue surface resulting in lost radiation. To save this reflected energy, the oral appliance of the present invention can include a highly reflective surface which will return at least a portion of the reflected radiation to the tissue. For example, the light emitting toothbrush pictured in FIG. 1 includes a reflective surface 20 for increasing radiation delivery efficiency. The tissue facing surfaces of the light emitting mouthpiece can similarly be reflective.

Figure 30:
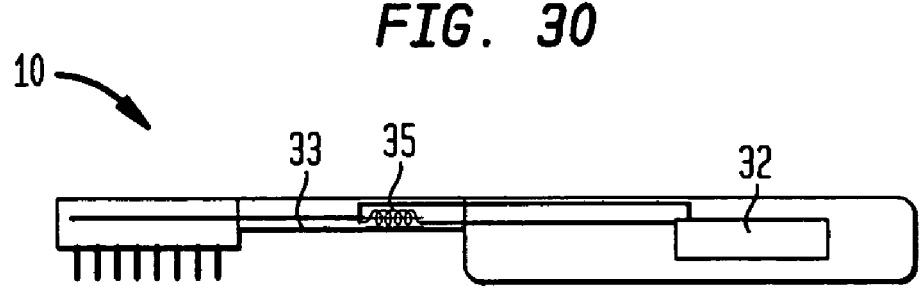
FIG. 30 illustrates another embodiment of the light emitting toothbrush of the present invention having electrical generating means.

The oral appliance of the present invention can include a power supply 32 (FIG. 28) for driving the light source and/or other components which may include a disposable battery, a rechargeable battery, and/or a solar battery in combination with a capacitor. Alternatively, the power can be partially or completely derived from the motion of the oral appliance. For example, FIG. 30 illustrates a light emitting toothbrush having a magnetic rod 33 movably disposed inside a coil 35. The back and forth motion of the light emitting toothbrush during brushing can generate electrical energy for supplying the electrical demands of the light source, other components, and/or a rechargeable battery.

An oral appliance according to the teachings of the invention can be employed for application of single-wise and/or multi-wise treatment procedures, e.g., twice per day for a few weeks or a month. The oral appliance of the present invention can be used with a variety of treatment agents, such as chromophores and optical couplers, to improve effectiveness. These agents can be part of an oral appliance system comprising a treatment agent for applying to the oral cavity and an oral appliance such as a light emitting toothbrush or a light emitting mouthpiece. In one embodiment, the treatment agent is applied to the oral cavity in the form of a paste, film, liquid rinse, spray, or combination thereof.

Chromophores (or photosensitizers) are useful as treatment agents for enhancing photodynamic and photothermal killing of microorganisms, as well as, tooth whitening and brightening. Chromophores include intrinsic light acceptors which induce and/or enhance chain-wise photochemical reactions leading to the generation of nitrogen oxide, singlet oxygen, and other radicals within tissue. Preferred chromophores include those which are nontoxic (i.e., those chromophores which can be provided at a concentration below which there is no action on bacteria or tissue without specific light). Exemplary exogenous chromophores for use in the present invention include dyes: methylene blue, indocyanine green, ALA- an inductor of porphyrins in proliferating cells-, mineral photocatalysts and photosensitizers: $TiO_2$, nanoparticles, fullerenes, tubulene, carbon black, and other similar treatment agents.

Endogenous chromophores are also present within the oral cavity and the surrounding tissue. These chromophores are naturally occurring substances which provide similar radical production to the exogenous species described above when exposed to optical radiation in their absorption band. Exemplary intrinsic chromophores include porphyrines like protoporphyrins, coproporphyrins, and Zn-protoporphyrins. The absorption band for porphyrins includes blue light, and to a lesser extent, green light and red light. Other intrinsic chromophores include cytochromes such as cytogem and cytoporphyrin, bilirubin, and molecular oxygen.

Figures 31, 32:
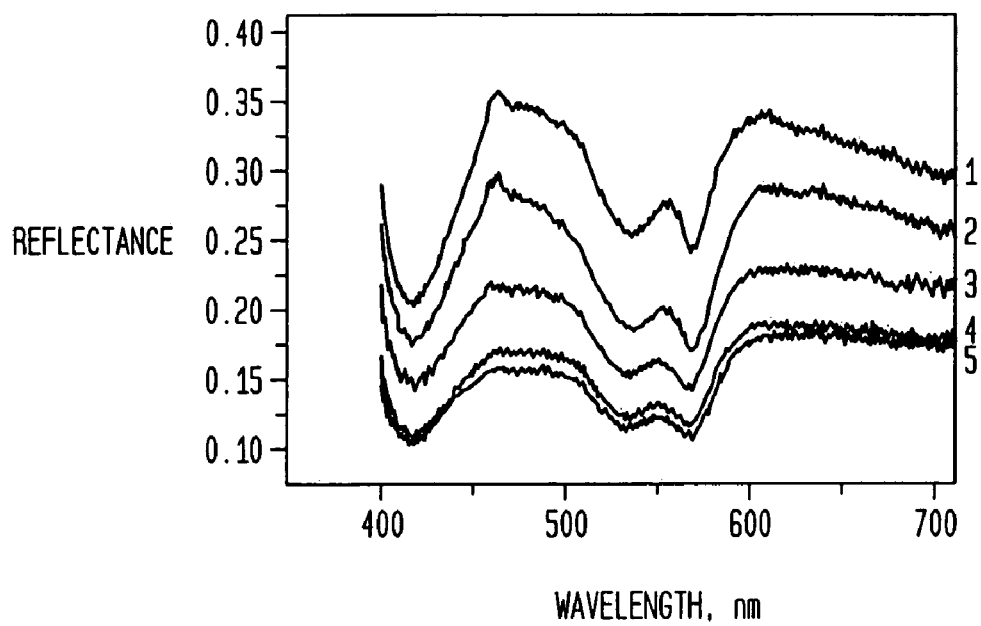
FIG. 31 illustrates a graph of reflectance versus wavelength.
FIG. 32 is a chart of optical coupling agents.

Another treatment agent which can be used with the present invention is an optical coupling agent. These compounds provide increased optical access into underlying tissue by reducing the amount of light scattering at the tissue surface. Exemplary optical coupling agents include glycerol; glucose; propylene glycol; polyethylene glycol; polyethylene glycol; x-ray contrasting agents (Trazograph-60, Trazograph-76, Verografin-60, Verografin-76, and Hypaque-60); proteins (hemoglobin, albumin); and combinations thereof. The optical coupling agents can also be used with additives such as ethanol and water (e.g., ethanol, glycerol and water). FIG. 31 illustrates a considerable reduction of backscattering (increasing of optical transmittance) of scleral tissue measured in vivo for a rabbit eye at administration of glucose solution by dropping. Due to similar structure of gingival tissue, the same optical coupling can be achieved in a few minutes (2–3 min) in a process of tooth cleaning using toothpaste containing an optical coupling agent. Some coupling agents, their refractive indices, and pH values are presented in FIG. 32. It is seen from FIG. 32 that the application of some optical coupling agents, besides effective reduction of scattering, can normalize pH within the oral cavity (6.5–6.9) and therefore minimize gingival and gum swelling.

Additional treatment agents may further include desensitizing agents (e.g., sodium citrate and potassium nitrate); gelling agents (e.g., sodium chloride and glycerol), sticky matrix materials (e.g., CARBOPPOL 974 NF); and conventional toothpastes. Materials which stabilize or adjust pH levels within the oral cavity may also be added as a treatment agent.

The oral appliance of the present invention can be used for a variety of photodynamic and phototherapeutic treatments in and around the oral cavity. These treatments are based on several biophysical phenomena that result from delivering light energy in the range of about 280 to 3000 nm with power densities in the range of about 1 to 10000 $mW/cm^2$ and are collectively referred to as biostimulation. In a preferred embodiment, biostimulation is effected with an energy flux in the range of about 1 $J/cm^2$ to 1000 $J/cm^2$, and in an even more preferred embodiment in the range of about 10 $J/cm^2$ to 100 $J/cm^2$.

Biostimulation can include, for example, increase in blood and lymph microcirculation of gingiva, tongue, salivary glands and ducts, tonsils, vocal cords, lips, cheeks, perioral facial skin, and other tissue due to light absorption by endogenous porphyrins, cytochroms, and tissue molecular oxygen. The light absorption can induce photo stimulated nitric oxide (NO) which causes dilatation of blood and/or lymph vessels and can also induce $Ca^{2+}$ storage in cell mitochondria and activation of $Ca^{2+}$-dependent ATPase in vascular smooth muscle cells which causes photo attenuated sympathetic vasomotor nerve activity. These processes activate a tissue drainage function; endothelium cells and endothelial leukocytes proliferative potency; and the formation of a new capillary net that helps regeneration of oral cavity epithelium, gingival tissue, neural tissue, skin collagen, and other tissue. In addition, the combined action of light therapy with heating can also cause activation of blood and lymph microcirculation of above mentioned tissues and glands.

Other effects include activation of blood microcirculation in tooth pulp due to light concentration in the tooth pulp caused by waveguide light propagation through enamel and dentin, and a corresponding increase in calcium ion flux from pulp to enamel through the protein matrix, which assists calcium ions to fill vacancies in the hydroxyapatite structure.

Biostimulation can also include an increase in local (oral and surrounding tissues) macrophage activity and fibroblast, osteoblast, and odontoblast proliferation. This can result in epithelium, collagen, nerve tissue, and hard tooth tissue regeneration. An additional important benefit can also be the killing of bacteria, fungi, and viruses. This effect is induced by light action on endogenous porphyrins, molecular oxygen, incorporated exogenous dyes, mineral photosensitizers, and/or mineral photocatalysts.

Another desirable effect is the normalization of oral cavity pH caused by bacteria activity reduction and oral lesions (stomatitis) healing which leads to decrease in oral tissue swelling and in osmotic pressure.

The systemic beneficial (biostimulation) effect can also provide improved immunocompetence via blood and lymph irradiation. In particular, biostimulation can cause light improved immunocompetence of blood and lymph macrophages, which produce superoxide and nitric oxide; erythrocyte membrane elasticity; and lymphocyte proliferation activity. Other whole body effects can include light-induced control of human circadian rhythms.

The oral appliances of the present invention can be used for a variety of other therapeutic treatments which include directly radiating areas of the oral cavity with optical radiation. Both the light emitting toothbrush and the light emitting mouthpiece can be used to radiate hard and/or soft tissue in the oral cavity with or without additional treatment steps such as heating, vibrating, and applying treatment agents such as chromophores and optical coupling agents.

In one embodiment the light emitting toothbrush and/or the light emitting mouthpiece can be used to treat dental problems such as gum bleeding, tooth hypersensitivity, tooth pain, bone problems, enamel degeneration, caries, root canal inflammation, and periodontal problems by radiating hard and/or soft oral tissue. The therapy can include directly radiating the problem area, and in some cases using heat or chromophores to assist with treatment.

As a further feature of the invention, the oral appliances can use multiple distinct wavelength bands as part of the therapy because multiple bands can provide, in some circumstances, a greater overall effectiveness. For example, while blue light is very effective at porphyrin excitation, the penetration depth of blue light is not high due to blood absorption and light scattering by biological tissue. By combining blue light with other wavelength bands, such as green and red which can more easily penetrate tissue, but which have less of a porphyrin exciting effect, the overall treatment can be made more effective. Multiple wavelength bands can also be used to excite different substances and produce biostimulation from several sources. In one embodiment, blue and green light can be used to stimulate porphyrins (400–430 nm) while redlight (e.g., 630 nm) and/or NIR (e.g., 1060 nm or 1268 nm) can be used to photoactivate molecular oxygen. In some cases, this results in a more effective overall treatment by relying on several therapeutic treatments providing a synergistic effect.

The oral appliances of the present invention also have an advantage because they can be used repeatedly at a low dose. Unlike high powered treatments which are performed a minimal number of times, the present invention can be used as part of the usual personal care regimen. The result is an overall dose which is effective to provide treatment, but which does not require the time and expense of visiting a doctor or dentist.

Therefore, the phototherapies provided by the oral appliances of the present invention can provide recovery and/or prophylaxes from a number of abnormalities and diseases. More specifically, the term "phototherapy" as used herein is intended to encompass both the treatment of abnormalities and also improvement of the user's physiology. Such beneficial improvements can further encompass both health and cosmetic improvements, as discussed below:

Dental

Reduction of gum bleeding. Gum bleeding is mostly caused by a poor proliferation of epithelial cells and other connective tissues. The oral appliances of the present invention can provide light irradiation and soft heating to activate increased fibroblast proliferation, causing regeneration of epithelium, collagen, and other connective tissue that helps stop gum bleeding. Light acceptors include endogenous porphyrins, cytochromes, and molecular oxygen and therefore irradiation of oral mucus and underlining tissue at power density of 1–1000 mW/cm$^2$ and daily doses of 0.06–30 J/cm$^2$ at the wavelengths corresponding to porphyrins, cytochromes, and molecular oxygen are preferred. Blue light (400–430 nm) is very effective for porphyrin excitation; green light (540–580 nm) and red light (600–650 nm) are also capable of activating porphyrins. In particular, coproporphyrins can be excited at the wavelengths: 402±20 (extinction at maximum≈480), 4950±20, 540±30 (extinction at maximum≈17), 580±30 (extinction at maximum≈6), 623±20 nm; and cytochroms: cytogem (the prosthetic group of cytochromoxidase) at 414±20 (extinction at maximum≈70), 439±20 (extinction at maximum≈117), 446±20 (extinction at maximum≈10), 534±20 (extinction at maximum≈11), 598±20 (extinction at maximum≈16), 635±20 nm (extinction at maximum≈9), and cytoporphyrin at 415±20 (extinction at maximum≈160), 520±20 (extinction at maximum≈9), 560±20 (extinction≈21), 580±20 (extinction at maximum 11), 617±20, 646±20 nm(extinction at maximum≈1)). Cytoporphyrin, which is found in bacteria, is very photosensitive. Protoporphyrin IX contained in bacteria and fungi can be excited at the wavelengths: 410±20 (extinction at maximum≈270), 504±20 (extinction at maximum≈15), 556±20 (extinction at maximum≈15), 600±20 (extinction at maximum≈6), 631±20 nm (extinction at maximum≈5)

Molecular oxygen can be photoactivated at the wavelengths 580±20, 630±20, 760±20, 1060±20, and 1268±20 nm. Moderate hyperthermia provided by a heater up to 43° C. during a tooth cleaning procedure of 0.5–3 min in duration is also desirable to provide a synergetic effect on blood and lymph microcirculation.

Reduction of tooth hypersensitivity. Tooth sensitivity results mostly from the increased movement of fluid through the dentinal tubes toward nerve endings in the tooth due to osmotic pressure induced by drink and/or saliva components. Tooth hypersensitivity depends on enamel porosity caused by temporal or permanent enamel demineralization induced by a low value of the oral liquid pH. At more acidic pH of the oral liquid (4.0–5.0), the enamel permeability increases 3–4-fold. Therefore, the process of enamel light-induced remineralization will assist in the reduction of tooth hypersensitivity. Bacteria killing will also lead to reduction of tooth hypersensitivity due to pH normalization and less gingival swelling and less osmotic pressure applied to hypersensitive tooth compounds. Therefore, irradiation of a tooth surface at a power density of 1–1000 mW/cm$^2$ and a daily dose of 0.06–30 J/cm$^2$ at wavelengths corresponding to porphyrins, cytochromes, and molecular oxygen are preferred. Blue light (400–430 nm) is very effective for bacterial porphyrin excitation; green light (530–580 nm) and red light (600–700 nm) are also capable of activating porphyrins in bacteria and killing them via radical generation. Green (540–580 nm) and red (600–650 nm) light are capable of activating tooth pulp porphyrins and increasing blood and lymph microcirculation in pulp, with a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a heater can also provide a synergetic effect on blood and lymph microcirculation. More effective bacteria killing can be accomplished by exogenous chromophore application and irradiation at wavelengths corresponding to the chromophore; in particular, for Methylene Blue (MB) dye at concentration of 0.01–1.0%, irradiation at 660±10 nm and power densities 5–1000 mW/cm$^2$; or for Indocyanine Green (ICG) dye at concentration of 0.01–1.0%, irradiation at 805±5 nm and power densities 5–1000 mW/cm$^2$.

Pain reduction in teeth is mostly due to improved pulpal blood and lymph microcirculation caused by dilatation of blood and/or lymph vessels induced by photo stimulated NO action on endothelial cells of vessel wall and by photo attenuated sympathetic vasomotor nerves activity. Direct light induced inhibition of nerve activity is also possible. Therefore, irradiation of a tooth surface at a power density of 1–1000 mW/cm$^2$ and a daily dose of 0.06–30 J/cm$^2$ at the wavelengths corresponding to porphyrins, cytochromes, and molecular oxygen are needed. Green (530–580 nm) and red light (600–650 nm) are capable of activating tooth pulp porphyrins and increasing blood and lymph microcirculation in pulp. Molecular oxygen dissolved in tissues and tooth pulp can be photoactivated at the wavelengths 580±20, 630±20, 760±20, 1060±20, and 1268±20 nm. Moderate hyperthermia provided by an electrical heater (or LED radiation heating) up to 43° C. during a tooth cleaning procedure of 0.5–3 min in duration is desirable to get a synergetic effect on blood and lymph microcirculation.

Periodontal and bone regeneration and implant connection are mostly caused by increase in macrophage activity, in fibroblast, osteoblast, and odontoblast proliferation, induced by light and/or combined light and thermal action. Increased blood and lymph microcirculation also improves tissue growing and regeneration. Irradiation of teeth and periodontal tissue at power density of 1–1000 mW/cm$^2$ and daily dose of 0.06–30 J/cm$^2$ at the wavelengths corresponding to porphyrins, cytochromes, and molecular oxygen will produce radicals responsible for increased macrophage activity, increased fibroblast, osteoblast, and odontoblast proliferation, and increased blood and lymph microcirculation. Blue light (400–430 nm) is very effective for porphyrin excitation; green light (530–580 nm) and red light (600–650 nm) are also capable of activating porphyrins. Green (530–580 rnm) and red light (600–650 nm) are capable of activating tooth pulp porphyrins. Molecular oxygen can be photoactivated at the wavelengths 580±20, 630±20, 760±20, 1060±20, and 1268±20 nm. Moderate hyperthermia provided by a special heater (or LED current heating) up to 43 ° C. during a tooth cleaning procedure of 0.5–3 min in duration is desirable to obtain a synergetic effect in macrophage activity, in fibroblast, osteoblast, and odontoblast proliferation, and increased blood and lymph microcirculation.

Remineralization of enamel. Enamel demineralization is induced mostly by a low value of the oral liquid pH. Light and soft heating activates blood and lymph microcirculation of gingiva and therefore increases calcium ion flux from saliva to enamel through the protein matrix; ions of calcium fill vacancies in hydroxyapatite structure. Bacteria killing leads to pH normalization and therefore prevents enamel demineralization. Therefore, irradiation of a tooth surface at a power density of 1–1000 mW/cm$^2$ and a daily dose of 0.06–30 J/cm$^2$ at the wavelengths corresponding to porphyrins, cytochromes, and molecular oxygen are needed. Blue light (400–430 nm) is very effective for bacterial porphyrin excitation; green light (530–580 nm) and red light (600–650 nm) are also capable of activating porphyrins in bacteria and killing them via radical generation. Green (530–580 nm) and red light (600–650 nm) are capable of activating tooth pulp porphyrins and increasing blood and lymph microcirculation in pulp and a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5–3 min in duration is desirable to get a synergetic effect on blood and lymph microcirculation. Sonophoresis and/or electrophoresis will assist in increasing blood and lymph flow, and in smoother distribution of Ca and P elements within hard tooth tissue. More effective bacteria killing (if needed) can be achieved by exogenous chromophore application and irradiation at wavelengths corresponding to the chromophore; in particular, for Methylene Blue (MB) dye at concentration of 0.01–1.0%, irradiation at 660±10 nm and power densities 5–100 mW/cm$^2$; or for Indocyanine Green (ICG) dye at concentration of 0.01–1.0%, irradiation at 805±5 nm and power densities 5–100 mW/cm$^2$.

Prevention of caries, which is usually caused mostly by Streptococcus mutants bacteria. Thus, bacteria killing via photodynamic effect induced by light and endogenous porphyrins, and/or cytochroms, and/or molecular oxygen, and/or exogenous dyes, and/or mineral photosensitizers, and/or mineral photocatalysts incorporated in the oral cavity, is a technique for caries prevention and healing. Light and thermal induced blood and lymph microcirculation in pulp and gingiva and increased calcium flux from saliva to enamel also prevents caries. Therefore, irradiation of a tooth surface at a power density of 1–1000 mW/cm$^2$ and a daily dose of 0.06–30 J/cm$^2$ at the wavelengths corresponding to porphyrins, cytochromes, and molecular oxygen are needed. Blue light (400–430 nm) is very effective for bacterial porphyrin excitation; green light (530–580 nm) and red light (600–650 nm) are also capable of activating porphyrins in bacteria and killing them via radical generation. Green (540–580 nm) and red light (600–650 nm) are capable of activating tooth pulp porphyrins and increasing blood and lymph microcirculation in pulp and a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5–3 min in duration is desirable to get a synergetic effect on blood and lymph microcirculation. Sonophoresis, and/or electrophoresis will assist in increasing blood and lymph flow, and in smoother distribution of Ca and P elements within hard tooth tissue. More effective bacteria killing (if needed) can be achieved by exogenous chromophore application and irradiation at wavelengths corresponding to the chromophore; in particular, for Methylene Blue (MB) dye at concentration of 0.01–1.0%, irradiation at 660±10 nm and power densities 5–100 mW/cm$^2$; or for Indocyanine Green (ICG) dye at concentration of 0.01–1.0%, irradiation at 805±5 nm and power densities 5–100 mW/cm$^2$. Very effective and nonspecific singlet oxygen and other radical production can be provided at broadband (300–900 nm) excitation of carbon nanoparticles or nanotubes, like carbon black, fullerene, or tubulene, and/or at application of a photocatalyst, like TiO$_2$ nanoparticles, in mixture with MB and/or ICG dyes.

Root canal sterilization and inflammation prevention also can be realized by photodynamic effect induced by light and endogenous porphyrins, in particular Protoporphyrin IX, and/or molecular oxygen, and/or exogenous dyes incorporated in tooth pulp via local blood and lymph microcirculation. Due to waveguide propagation, light is concentrated in the tooth pulp, and therefore enhances photodynamic efficiency and activates pulp blood and lymph microcirculation. Light also improves immunocompetence of macrophages, which produce SO and NO responsible for host defense against microorganisms. Therefore, irradiation of a tooth surface at a power density of 1–1000 mW/cm$^2$ and a daily dose of 0.06–30 J/cm$^2$ at the wavelengths corresponding to porphyrins, cytochromes, and molecular oxygen are needed. Green (540–580 nm) and red (600–650 nm) light are capable of activating tooth pulp porphyrins to produce radicals for bacteria killing, improvement of macrophage immunocompetence, and increased blood and lymph microcirculation in pulp. Molecular oxygen dissolved in tissues and tooth pulp can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5–3 min in duration is desirable to get a synergetic effect on blood and lymph microcirculation. Sonophoresis and/or electrophoresis will assist in increase of blood and lymph flow. The light which penetrates to the root canal and apex area can prevent or decrease inflammation associated with bacteria growth Periodontal problem prevention and healing is also due to the lethal effect of light on bacteria via excitation of endogenous porphyrins, and/or molecular oxygen, and/or exogenous dyes, and/or mineral photosensitizers, and/or mineral photocatalysts incorporated in the periodontal lesions via production of active (singlet) oxygen and other radicals. Light also improves immunocompetence of macrophages, which produce SO and NO responsible for host defense against microorganisms. Light and soft heating activate blood and lymph microcirculation and therefore activate endotheliocytes proliferative potency and formation of new capillary net that helps to keep gingiva attached to the teeth. Therefore, light power densities, daily doses, and wavelengths are the same as used for prevention of caries (see, Prevention of caries).

Soft Tissue Treatments:

Another advantage of the oral appliances of the present invention is that they allow directional radiating. In some cases discussed below it is desirable to optically radiate primarily soft tissue such as tongue tissue, nerve tissue, throat tissue, vascular tissue, hair follicles, sebaceous follicles, sebaceous glands, facial subcutaneous fat, facial muscular tissue, lymph systems, collagen, pigmented spots, and/or other tissue including other facial tissue and other oral tissue. The oral appliances allow for directing radiation toward these tissue areas by choosing the direction in which the optical radiation is emitted. For example, to radiate facial tissue, the optical radiation source can be positioned on the outer perimeter of a light emitting toothbrush or a light emitting mouthpiece. Unlike conventional toothbrushes which only radiate in the direction of the bristle (toward the hard tissue of the teeth), the radiation provided by theseappliances can be directed such that the emitted radiation penetrates the mucosal lining of the oral cavity to deliver phototherapy to a region within the user's soft facial tissue.

In addition, the oral appliances of the present invention allow certain conditions, which had in the past been treated from outside the oral cavity, to be treated by employing an optical radiation source from within the oral cavity. For example, instead of treating acne by radiating the effected skin, the oral appliances can directly radiate from within the oral cavity out toward the target tissue. This is advantageous because the tissue within the oral cavity is easier to penetrate due to the limited amount of collagen contained in the tissue walls of the oral cavity. As a result, optical energy more easily penetrates tissue to provide treatment at a lower level of energy and reduce the risk of tissue damage. Preferable range of wavelength for this type of treatment is in the range of about 280 nm to 1400 nm and even more preferably in the range of about 590 nm –1300 nm.

Improvement of oral mucus inflammatory disease (stomatitis—superficial erosions and fissuring at the angle of the mouth, an acute infection of the oral mucosa with vesicle formation, due to the herpes simplex virus, stomatitis with shallow ulcers on the cheeks, tongue, and lips) due to lethal effect of light on viruses and bacteria via excitation of endogenous porphyrins, and/or molecular oxygen, and/or exogenous dyes, and/or mineral photosensitizers, and/or mineral photocatalysts incorporated in the oral mucus lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Light power densities, daily doses, and wavelengths are the same as used for prevention of caries (see, Prevention of caries).

Tongue diseases (black tongue—the presence of a brown fur-like patch on the dorsum of the tongue, composed of hypertrophied filiform papillae with microorganisms and some pigment; coated tongue—one covered with a whitish or yellowish layer consisting of desquamated epithelium, debris, bacteria, fungi, etc.) improvement due to lethal effect of light on microorganisms via excitation of endogenous porphyrins, and/or molecular oxygen, and/or exogenous dyes, and/or mineral photosensitizers, and/or mineral photocatalysts incorporated in the tongue lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Llight power densities, daily doses, and wavelengths are the same as used for prevention of caries (see, Prevention of caries).

Recovery from inflammation of salivary glands and small sublingual ducts, which open into the mouth on the sublingual fold (ducts of Rivinus). The same mechanisms of recovery as for stomatitis and tongue lesions are expected. Light power densities, daily doses, and wavelengths are the same as used for prevention of caries (see, Prevention of caries).

Pain reduction in oral tissue results mostly from improved blood and lymph microcirculation caused by dilatation of blood and/or lymph vessels induced by photo stimulated NO action on endothelial cells of vessel wall and by photo attenuated sympathetic vasomotor nerves activity. Direct light induced inhibition of nerve activity is also possible. Light power densities, daily doses, and wavelengths are the same as used for dental pain reduction (see, Pain reduction in teeth).

Improvement of sore throat, angina, acute or chronic tonsillitis, etc. caused mostly by growth of *Staphylococcus aureus* bacteria (tonsillitis inflammation of tonsils, especially the palatine tonsils; follicular tonsillitis, tonsillitis especially affecting the crypts; parenchymatous tonsillitis; acute tonsillitis, that affecting whole substance of the tonsil; pustular tonsillitis, a variety characterized by formation of pustules). Such improvement is due to lethal effect of light on bacteria via excitation of endogenous porphyrins, and/or molecular oxygen, and/or exogenous dyes, and/or mineral photosensitizers, and/or mineral photocatalysts incorporated in tonsil lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Light power densities, daily doses, and wavelengths are the same as used for prevention of caries (see, Dental, 6). ALA related treatment with low concentration of ALA, an inductor of porphyrins in proliferating cells, at 620–640 nm excitation can be used for suppression of abnormal proliferation or oral mucous epithelial cells, glands growing, microbial colonies within oral tissues (gingival, glands, tongue, throat, etc). In particular, treatment of pharyngomycosis can be provided.

Sinusitis caused mostly by *Steptococcus pneumoniae* bacteria. The same mechanisms of recovery as for angina and tonsillitis. Light power densities, daily doses, and wavelengths are the same as used for prevention of caries (see, Prevention of caries).

Recovery from laryngitis and other inflammations of the vocal cords. The same mechanisms of recovery as for angina, tonsilities, and sinusities. Light power densities, daily doses, and wavelengths are the same as used for prevention of caries (see, Prevention of caries).

Improvement of skin texture, elasticity, as well as wrinkle reduction (i.e., skin rejuvenation) around lips and cheeks via increased macrophage and fibroblast proliferation activities and new collagen production induced by light and/or combined light and thermal action. Increased blood and lymph microcirculation also improves tissue growth and regeneration. Light power densities, daily doses, and wavelengths are the same as used for periodontal and bone regeneration and implant connection (see, Periodontal and bone regeneration and implant connection).

Improvement of acne. Due to high penetration depth of red light, it is possible to provide needed irradiation dose to sebaceous glands through cheek tissues for a lethal light effect on acne causing bacteria concentrated within the sebaceous glands. The light excitation of bacteria porphyrins will generate active (singlet) oxygen and other radicals which selectively kill these bacteria. Therefore, irradiation of cheeks inside the oral cavity at a power density of 1–1000 mW/cm$^2$ and a daily dose of 0.06–30 J/cm$^2$ at the wavelengths corresponding to bacterial porphyrins is desirable. Green (530–580 nm) and red light (600–650 nm) can penetrate through cheek tissue and activate acne bacterial porphyrins to produce radicals which kill bacteria. The acne treatment efficiency can be enhanced by application of an appropriate photosensitizer (e.g., methylene blue, indocyanine green, ALA, etc) to the acne lesion in combination with utilizing red and/or NIR radiation.

Hair growth control can be provided by normalization of blood and lymph microcirculation within hair follicles by light, and/or combined light and thermal action. Irradiation of oral cavity tissues at a power density of 1–1000 mW/cm$^2$ and a daily dose of 0.06–30 J/cm$^2$ at the wavelengths corresponding to porphyrins, cytochromes, and molecular oxygen will produce radicals responsible for vessel dilatation and corresponding increase of blood and lymph microcirculation. Green (530–580 nm) and red light (600–650 nm) penetrate through cheek tissue and activate porphyrins and cytochromes. Molecular oxygen can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5–3 min in duration is desirable to get a synergetic effect in increase of blood and lymph microcirculation. Hair growth control can, for example, includes hair removal or reduction by selective destruction of multiple hair follicles using a single or time-dependent sequence of radiation.

Vascular improvement can be associated with increased macrophage and fibroblast proliferation activities and new collagen and epithelium production induced by light and/or combined light and thermal action. Irradiation of oral cavity tissues at a power density of 1–1000 mW/cm$^2$ and a daily dose of 0.06–30 J/cm$^2$ at the wavelengths corresponding to porphyrins, cytochromes, and molecular oxygen will produce radicals responsible for increase in macrophage activity, fibroblast proliferation, and collagen growth. Green (530–580 nm) and red light (600–650 nm) penetrate through cheek tissue and activate tissue porphyrins and cytochroms. Molecular oxygen can be photoactivated at the wavelengths 580±20, 630±20, 760±20, 1060±20, and 1268±20 nm. Moderate hyperthermia provided by a special heater (or LED current heating) up to 43 ° C. during a procedure of 0.5–3 min in duration is desirable to get a synergetic effect in macrophage activity, fibroblast proliferation, and collagen growth.

Perioral dermatitis treatment is due to light improved immunocompetence of macrophages, and light activated blood and lymph microcirculation caused epidermal cell proliferative potency. Irradiation of oral cavity tissue at a power density of 1–1000 mW/cm$^2$ and a daily dose of 0.06–30 J/cm$^2$ at the wavelengths corresponding to porphyrins, cytochromes, and molecular oxygen will produce radicals responsible for increased macrophage activity and increased blood and lymph microcirculation. Green (530–580 nm) and red light (600–650 nm) penetrate through cheek tissue and activate porphyrins and cytochroms. Molecular oxygen can be photoactivated at the wavelengths 580±20, 630±20, 760±20, 1060±20, and 1268±20 nm. Moderate hyperthermia provided by a special heater (or LED current heating) up to 43° C. during a procedure of 0.5–3 min in duration is desirable to get a synergetic effect in macrophage activity and increase of blood and lymph microcirculation.

Repair of damaged trigeminal facial nerve peripheral receptors in the oral cavity tissues, including gingiva, teeth, lips, and tongue, and other nerves controlling oral tissue functioning, can be caused by $Ca^{2+}$ storage in neural cell mitochondria and followed activation of $Ca^{2+}$-dependent ATPase in these cells. Increase of blood and lymph microcirculation induced by light and/or combined light and thermal action also should be important for neural tissue regeneration. Light power densities, daily doses, and wavelengths are the same as used for perioral dermatitis treatment (see, perioral facial skin).

Pain reduction in oral tissue results mostly from improved blood and lymph microcirculation caused by dilatation of blood and/or lymph vessels induced by photo stimulated NO action on endothelial cells of vessel wall and by photo attenuated sympathetic vasomotor nerve activity. Direct light induced inhibition of nerve activity is also possible. The following nerves may be involved in the process: buccal nerve which innervate oral mucosa and cheek skin at the mouth nook; inferior and superior alveolar nerves which innervate teeth, periosteum and gingiva; glossopharyngeal, hypoglossal, and lingual nerves, which innervate gullet, tongue and chin-tongue muscles, and oral cavity bottom mucosa; inferior, recurrens, and superior laryngeal nerves which innervates gullet muscles and mucosa; masseteric nerve which innervates masticatory muscle. Light power densities, daily doses, and wavelengths are the same as used for dental pain reduction (see, Pain reduction in teeth).

Beneficial influence on human organism immunocompetence, in particular by light improved immunocompetence of blood and lymph macrophages, which produce superoxide and nitric oxide; erythrocytes membrane elasticity and lymphocyte proliferation activity. Light acceptors are endogenous porphyrins, cytochroms, and molecular oxygen. Therefore, irradiation of oral mucus and underlying tissue, well supplied by blood vessels, should be at power density of 1–1000 mW/cm$^2$, daily doses of 0.06–30 J/cm$^2$ and at the wavelengths corresponding to porphyrins, cytochromes, and molecular oxygen. Blue light (400–430 nm) is very effective for porphyrins excitation; green light (530–580 nm) and red light (600–650 nm) are also capable to activate porphyrins. In particular, coproporphyrins can be excited at the wavelengths: 402±20 (extinction at maximum≈480), 495±20, 540±30 (extinction at maximum≈17), 580±30 (extinction at maximum≈6), 623±20 nm; and cytochroms: cytogem at 414±20 (extinction at maximum≈70), 430±20 (extinction at maximum≈117), 446±20 (extinction maximum≈10), 534±20 (extinction at maximum≈11), 598±20 (extinction at maximum≈16), 635±20 nm (extinction at maximum≈9), and cytoporphyrin (porphyrin a) at 415±20 (extinction at maximum≈160), 520±20 (extinction at maximum≈9), 560±20 (extinction≈21), 580±20 (extinction at maximum≈11), 617±20, 646±20 nm (extinction at maximum≈1). Protoporphyrin IX can be excited at the wavelengths: 410±20 (extinction at maximum≈270), 504±20 (extinction at maximum≈15), 556±20 (extinction at maximum≈15), 600±20 (extinction at maximum≈6), 631±20 nm (extinction at maximum≈5) Molecular oxygen can be photoactivated at the wavelengths 580±20, 630±20, 760±20, 1060±20, and 1268±20 nm.

Control of circadian rhythms. Blue light at 470 nm affects the circadian rhythms of humans and might be applicable to anyone who has biological rhythms disorder. The possible light acceptors are blood bilirubin and/or coproporphyrins. Light irradiation of oral mucus and underlining tissue, well supplied by blood vessels, is desirably at power density of 1–1000 mW/cm$^2$, one-day dose of 0.06–30 J/cm$^2$ and wavelengths corresponding to bilirubin absorption (455±20 nm) and/or Coproporphyrins I and III absorption (402±20, 470±20, 540±30, 580±30, 623±20 nm). In some embodiments of the invention, a light-emitting toothbrush is provided that can be utilized to irradiate the user's oral cavity in the morning with radiation having a selected wavelength, e.g., blue light (or other biostimulating light), and to irradiate the oral cavity in the evening with radiation having another wavelength, e.g., red light (or light having a sedative effect), so as to help regulate the user's circadian cycle.

Controllable destruction of metabolic components of blood, in particular bilirubin, appearing in the blood stream due to normal or pathological decay of erythrocytes, allows for prevention of such diseases as bilirubinemia. Light irradiation of oral mucus and underlining tissue, well supplied by blood vessels at 450–460 nm with power density of 1–1000 mW/cm$^2$ and one-day dose of 0.06–30 J/cm$^2$ is preferable.

Killing viruses within the blood microcirculatory system via photodynamic effect by topical application (e.g., to oral mucous) or intravenous injection of an appropriate photodynamic agent like ALA, hematoporphyrin, etc. Light irradiation of oral mucus and underlining tissue, well supplied by blood vessels, for this treatment should be preferably at a power density of 1–1000 mW/cm$^2$, one-day dose of 0.06–30 J/cm$^2$ and wavelengths corresponding to absorption spectra of the photodynamic agent which is used. For ALA application, these wavelengths correspond to absorption bands of Protoporphyrin IX (409±20, 503±20, 538±20, 555±20, 576±20, 600±20, 632±20 nm); while for Hematoporphyrin derivatives (HPD) the wavelength is 620±20 nm.

Diseases of the lip can also be treated light and/or combined light and thermal action. Irradiation of oral cavity tissues at a power density of 1–1000 mW/cm$^2$ and a daily dose of 0.06–30 J/cm$^2$ at the wavelengths corresponding to porphyrins, cytochromes, and molecular oxygen will produce radicals responsible for increase in macrophage activity, fibroblast proliferation, and collagen growth. Green (530–580 mn) and red light (600–650 mn) penetrate through cheek tissue and activate tissue porphyrins and cytochroms. Molecular oxygen can be photoactivated at the wavelengths 580±20, 630±20, 760±20, 1060±20, and 1268±20 nm. Moderate hyperthermia provided by a special heater (or LED current heating) up to 43° C. during a procedure of 0.5–3 min in duration is desirable to get a synergetic effect in macrophage activity, fibroblast proliferation, and collagen growth.

Drug delivery. Radiating soft tissue within the oral cavity, and particularly the area under the tongue, can improve the efficiency of drug delivery into the blood stream. The optical radiation creates NO species which in turn causes blood vessel to dilate and can thereby increase the absorption rate and efficiency of pharmaceutical agents placed on the tissue surface. In one embodiment a drug is placed under the tongue and optical radiation is directed toward the adjacent soft tissue. Another more complex drug delivery involves in situ activation of chemical therapeutic components, which in an inactive state can readily diffuse into the oral cavity tissue, by radiation. For example, such agents in an inactive form can be administered to a patient's oral cavity tissue followed by activation via irradiation at a selected wavelength.

Figure 33:
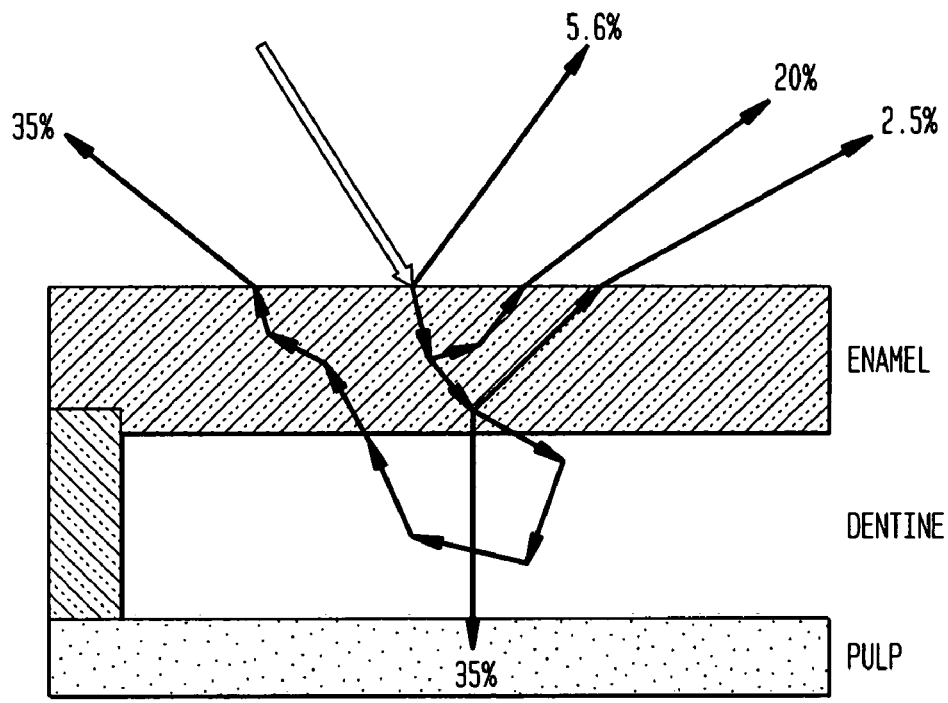
FIG. 33 is a schematic of light entry into tooth structure.

Another use for the oral appliances of the present invention is tooth whitening and brightening. All current tooth whitening technologies are based on chemical bleaching effects of peroxides. Tooth color is defined by its structure and optical properties of acquired pellicle, enamel, dentin. All these components are generally responsible for presenting a stained appearance. FIG. 33 shows exemplary light distribution within a tooth. Note that over 30% of the light reaches the dentine and over 30% of the light reaches the tooth pulp. Cosmetic appearance of the tooth depends on reflection from enamel and dentine. Extrinsic and/or intrinsic staining results in tooth color. Usually, compounds such as tannins, other food pigments, and poly-phenolic components of smoke which become trapped in and tightly bounded to the proteinaceous layer on the surface of the teeth cause extrinsic staining of the acquired pellicle, and typically can be removed mechanically using a toothbrush. Natural color of a tooth is determined by the light scattering and absorption properties of dentine and enamel-dentine junction. With aging, many proteins, including collagen, contained in dentin become more yellowish due to changes in molecular structure. Such age-dependent coloration is an example of intrinsic coloration. For heavy smokers, coffee drinkers and red wine drinkers, food colorants may penetrate in tooth depth, in enamel and even dentin, and therefore could not be removed by mechanical cleaning, and should be considered as intrinsic. Some systematic lesions caused by a surplus of fluorine in drinking water or by prolonged usage of tetracycline are other examples of intrinsic colorants. To bleach intrinsic tooth stains, chemical methods, based on oxidation or enzymes application are usually used.

Use of optical radiation from the oral appliances of the present invention can provide effective tooth whitening and brightening. An additional benefit from using a light emitting toothbrush can be concurrent prophylaxis and/or treatment in the user's home of periodontal disease, caries and other oral diseases, which are based mostly on effective bacteria killing and lesion healing.

The oral appliance can provide optical teeth whitening and brightening based on the following exemplary mechanisms of color centers bleaching in enamel and dentin; 1) short wavelength (300–500 nm) direct photobleaching; 2) wavelengths in the range 960±20 nm, and/or 1200–12000 nm, more preferably 1450±150 nm, and/or 1890±250 nm and/or 2400–3200 nm; 9000–12000 nm are used for photo thermal bleaching; and 3) direct photo and photochemical production of singlet oxygen within enamel and dentin using light absorption by oxygen in tissue at 580±20, 630±20, 760±20, 1060±20, and 1268±20 nm, and/or light absorption at selective wavelengths in the range 300–900 nm corresponding to absorption bands of a photosensitizer due to a photodynamic effect upon endogenous and/or externally applied photosensitizers and/or photocatalysts (FDA approved dyes, and/or carbon black (graft copolymers), fullerenes (carbon nanoparticles), and/or tubulenes (carbon nanotubes), and/or $TiO_2$ nanoparticles).

Figure 34:
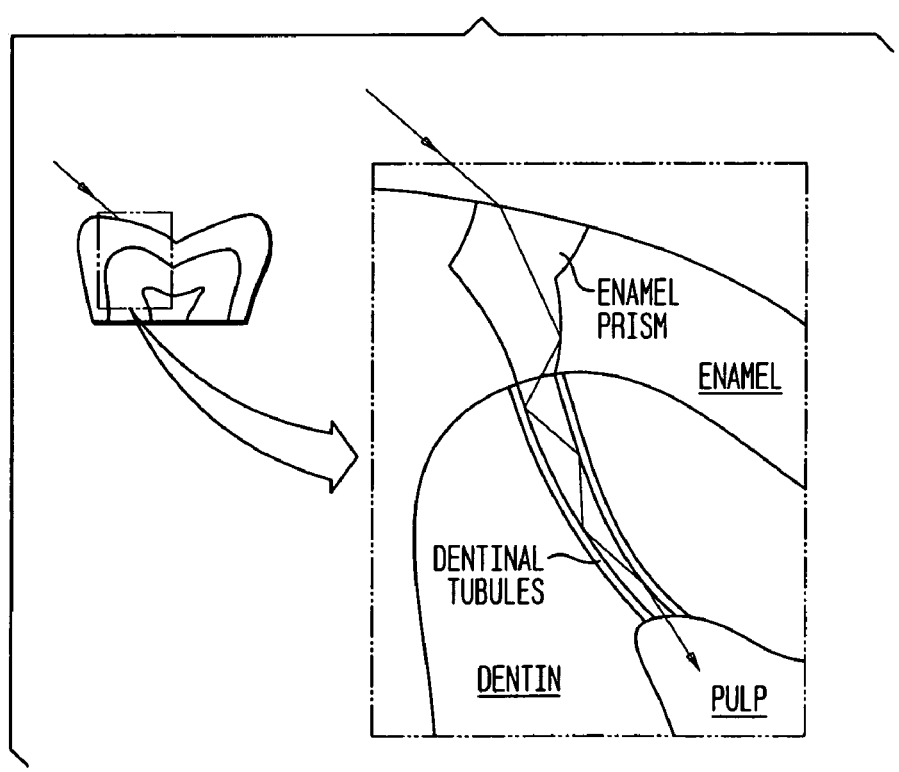
FIG. 34 illustrates the entry of radiation into tooth enamel, dentine, and pulp.

FIG. 34 illustrates tooth structure and light paths within enamel and dentine due to the waveguide effect of enamel prisms and dentinal tubes. In one aspect, the present invention takes advantage of this effect to direct radiation deep into the tooth to treat intrinsic stains in the dentine structure and the pulp. In some embodiments, an oral appliance of the present invention optically radiates stains within the dentine. One of the main advantage of this invention is the possibility to produce active radicals like singlet oxygen not only on the tooth surface, but also depth in hard tissue (enamel and dentin), and therefore effectively bleach intrinsic colorants. The waveguiding (photonic crystal) structure of dentin gives the possibility to concentrate light within narrow dentin tubules (1–5 µm in diameter) filled by water and odontoblast surrounded by organic (collagen) materials. The specific feature of this invention to bleach bulky light absorbers provides not only tooth whitening, but also tooth brightening due to a decrease in bulk absorption of light and an increase in back scattering. Photobiostimulation can also be employed to cause new dentine growth by radiation targeting of odonoplast and pulp, thereby enhancing cosmetic appearance of deep tooth structure. Further, utilizing low dose radiation every day can cause tooth rejuvenation.

In another embodiment, the optical appliance of the present invention is used to irradiate teeth so as to reduce staining within the dentine and the enamel; the teeth are thereby whitened and brightened. In one embodiment, teeth are optically radiated with radiation in the wavelength band between approximately 300 and 1350 nm. The oral appliance can also include a mechanical vibrator for better cleaning, and/or electrodes for electrophoresis of the photosensitizer. In addition, a photodetector and a microchip for detection of reflected and/or fluorescent light from enamel can be used to monitor tooth color.

Heating with electrical heaters or with radiation in the wavelength range above about 800 nm to about 100000 nm (100 microns) can be used to facilitate whitening and brightening. The use of optical radiation is particularly advantageous because it allow for deep, selective heating. By choosing an appropriate wavelength, the tooth can be heated to a predetermined depth and color centers can be destroyed and removed from enamel due to thermally induce bleaching and diffusion. The stain will diffuse out of the tooth and can be dissolved in saliva or saline (if present). Prefered wavelength ranges include 960±20 nm, and/or 1200–100000 nm; more preferably 1450±150 nm, and/or 1890±250 nm and/or 2400–3200 nm.

The oral appliances of the present invention can also directly photobleach teeth using only intrinsic light absorbers. Alternatively, the exogenous chromophores discussed above can be use to improve the effectiveness of tooth whitening and brightening. The chromophores (and other treatment agents) can be applied to teeth and then the teeth irradiated.

Direct experimental modeling has been done of the efficiency of MB and red light irradiation for bleaching of foreign pigments caused by tea, coffee, or red wine action. As a suitable model, acrylic plastic material used for denture prosthesis was chosen. Slabs of 3 mm in thickness were used. Staining of slabs was performed via dropping of tea, coffee, or red wine, and followed natural drying of the sample for 1–2 hours. It was important for photobleaching that the sample should be not be absolutely dry, some wetness should remain.

A simpler model providing a quick preparation period was based on usage of a high quality white paper. For such model, a few drops of a solution of tea, coffee, or red wine for a few minutes of application were enough. After preparation of the described experimental models of stained tooth, photobleaching experiments were done. First, the stained samples were impregnated by a 1% MB dye water solution during a few minutes. The back reflectance spectra of such samples were measured in the range from 400 to 800 nm using a fiber optic CCD grating spectrometer LESA-7. These spectra served as a baseline for photobleached samples. Photobleached samples were received at irradiation during 10 min by a He—Ne laser (633 nm) providing power density of 20 mW/cm$^2$.

Figure 35:
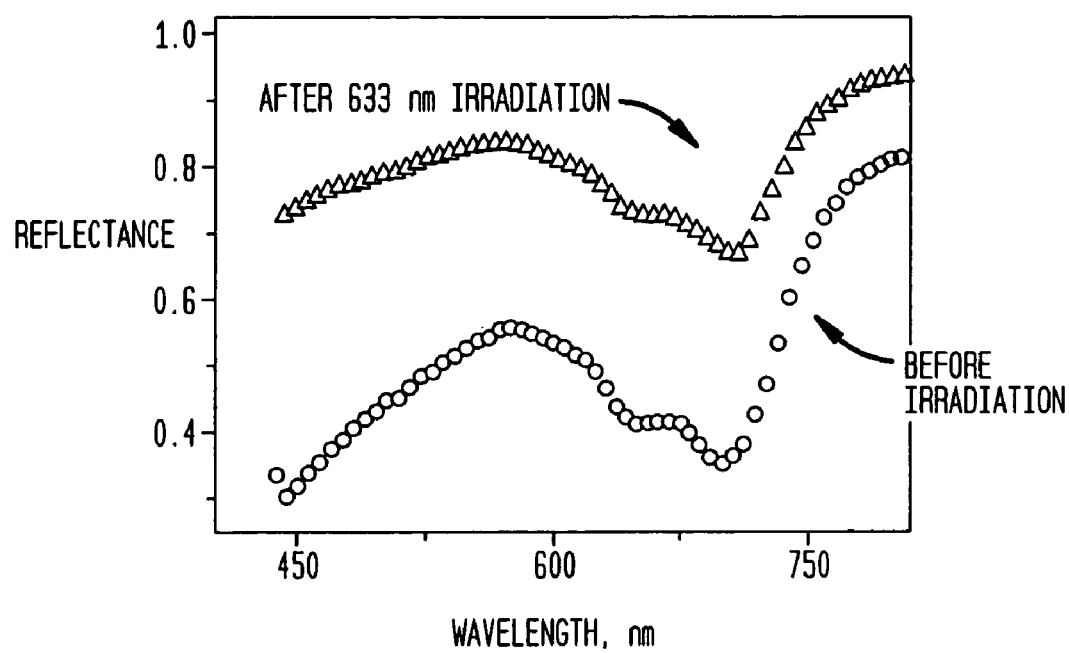
FIG. 35 is a graph of reflectance versus wavelength before and after irradiation.
Figure 36:
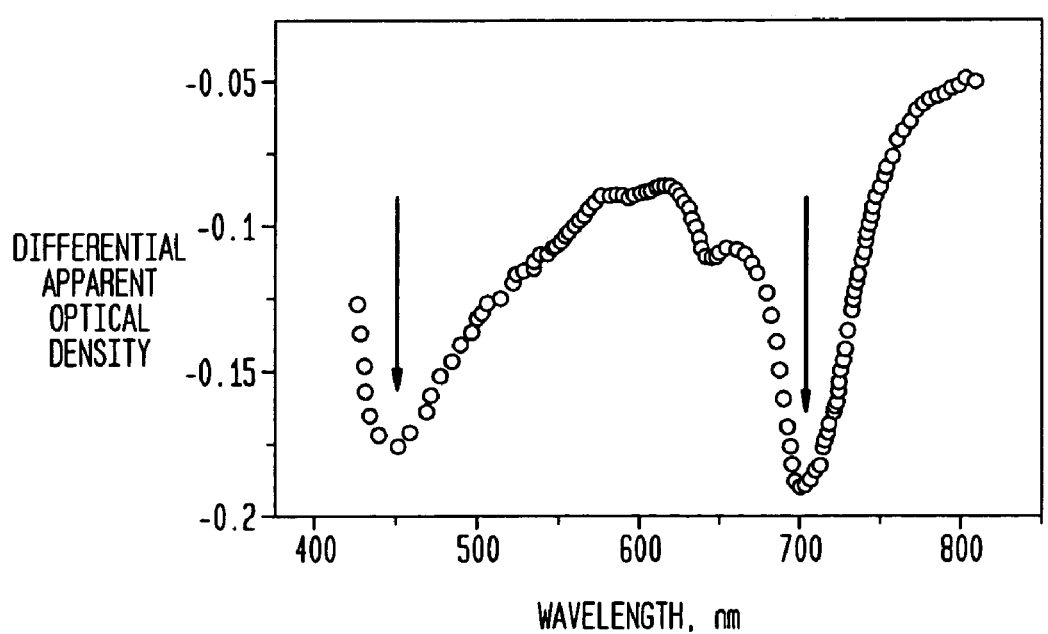
FIG. 36 is a graph of differential apparent optical density versus wavelength.

Results for coffee stains are shown in FIGS. 35 and 36. Spectrum received before irradiation shows absorption bands of coffee with maximum at 450 nm and MB with two maximums around 650 nm. After 10 minutes of laser irradiation, the spectrum is dramatically changed. Due to photobleaching of both cromophores, and thus much less absorption by coffee extract and MB, the spectrum becomes smooth with about twice higher reflection (scattering) in the visible range. Therefore, whitening and brightening of the sample occurred.

The differential apparent optical density spectra presented in FIG. 36 allows one to evaluate photobleaching efficiency, which is much greater for the absorption bands of coffee extract and MB. The negative values imply that reflectance of the model increases under irradiation.

It should be noted that for all tested food pigments (coffee, tea, and red wine) similar results were received. The white paper model also works well and can be recommended for the fast testing of photosensitizer activity to bleach a target stain of different origin.

In another embodiment, dentine stains can be selectively photobleached by direct optical radiation within the absorption range of the stain. Unlike conventional tooth whitening, the present invention allows a user to use select wavelength ranges centered around the absorption spectrum of the stain, which can be in a range of about 280 to about 800 nm. The result is whitening and brightening with a very specific wavelength band.

Figure 37:
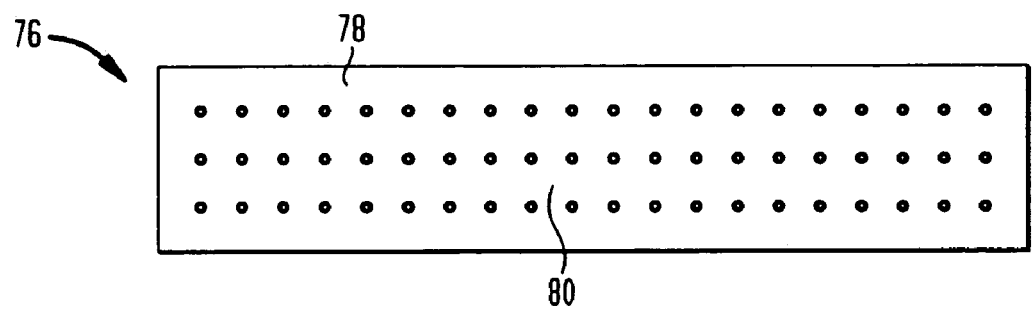
FIG. 37 illustrates a tooth whitening strip for use with the light emitting oral appliance of the present invention.

With reference to FIG. 37, in another aspect, the invention provides a tooth-whitening strip 76 formed as a flexible thin film 78 that incorporates at least one chromophore 80, which can be activated by radiation of suitable wavelength. The thin film 78 is sufficiently flexible to allow its placement over a subject's teeth, and can preferably include adhesives known in the art to facilitate its in contact with the teeth during a treatment session. The thin film 78, which can be formed by employing material known in the art, can have a thickness in a range of about 20 to about 1500 microns, and more preferably, in a range of about 50 to about 1000 microns. In some embodiments, the thin film is a polymeric matrix, e.g., a matrix of ethylene oxide, that can optionally include a plasticizer, e.g., propylene glycol or polyethylene glycol. The chromophore 80, which is preferably a non-peroxide chromophore, can be, for example, any of the chromophores described above for tooth whitening. The chromophore 80 can be incorporated in the thin film 78 in a variety of different ways. For example, it can be dispersed within the polymeric matrix of the film, or be disposed as a thin layer over a film's surface.

In another aspect of the invention, biostimulating and/or dental phototherapies are disclosed for conditions that are normally responsive to a known power density of phototherapeutic radiation (1–10 treatments spaced 1–30 days). However, in the present invention a series of temporally spaced treatment sessions are delivered to a patient, where each session provides a power density of therapeutic radiation lower than typical power density needed to treat the condition according to the conventional protocols. The method can comprise the steps of selecting a condition normally responsive to oral application of a known power density of phototherapeutic radiation, and delivering a series of temporally spaced treatment sessions to a patient. Each session provides a power density of therapeutic radiation lower than the typical power density needed to treat the patient condition. The series of temporally spaced treatment sessions can be continued until the patient's condition is ameliorated by a cumulative effect of the series of treatment sessions. The power density applied to the patient's skin surface is between approximately 1 mW/cm$^2$ and approximately 100 W/cm$^2$, and depends at least on the condition being treated and the wavelength of the radiation. Preferably, the energy at the tooth or muscosal surface is between 10 mW/cm$^2$ and 10 W/cm$^2$. The radiation can be applied for a duration of one second to one hour. Energy flux can be in the range of about 1 J/cm$^2$ to 1000 J/cm$^2$, and preferably in the range of about 10 J/cm$^2$ to 100 J/cm$^2$. In many embodiments, an emitting area of an LETM or LEMP can be in a range of about 0.1 to about 100 cm$^2$ and the power delivered is in a range of about 1 mW to about 10 W, and preferably in a range of about 10 mW to about 1 W. This power can be delivered by employing highly efficient light sources, such as those described above, with power supplies that can be as small as a batter, or wall plug power supplies.

Figure 38:
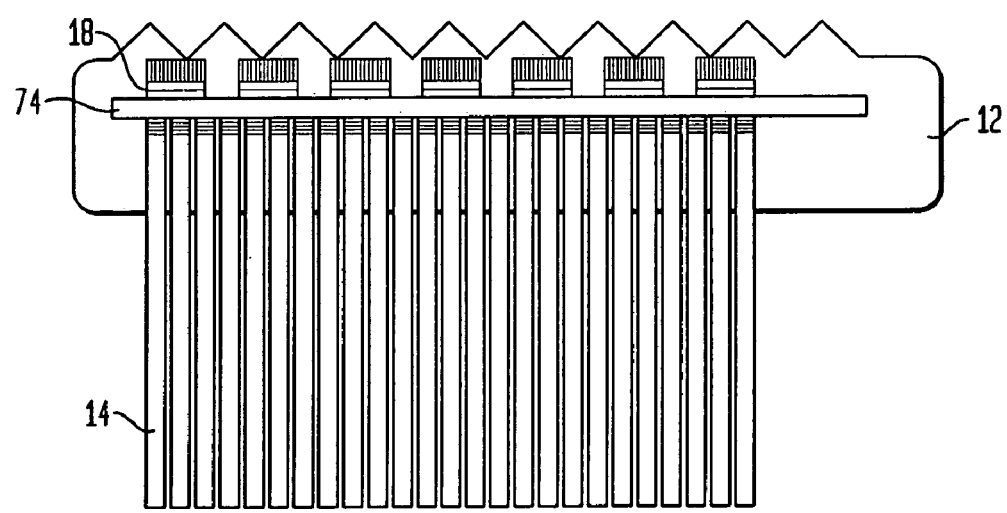
FIG. 38 illustrates another embodiment of the light emitting oral appliance of the present invention.

A variety of manufacturing techniques can be employed for form a light-emitting appliance according to the teachings of the invention. For example, with reference to FIG. 38, the plurality of light-emitting sources 18 can be formed epitaxially over substrate 74, for example, a GaAS substrate, in a manner known in the art. For example, each light source can be formed as a semiconductor heterostructure having repeat units whose compositions are selected in a manner known in the art to generate radiation within one or more desired wavelength bands. Additional light sources emitting radiation in a direction substantially parallel to the bristles can also be formed on an opposed side of the wafer in a similar manner. The bristles 14 can be coupled to the substrate surface either directly, or via intervening elements. The substrate can then be housed at least partially within a portion of the brush head 12, which is preferably formed of a material that is substantially transparent to radiation generated by the sources. The material forming the brush head also preferably exhibits a high thermal conductivity to facilitate cooling of the radiation sources. LED structure can be cleaved from the wafer as 2D matrix of individual LEDs or as ID bar of LED similar to a diode laser bar. In another embodiments, the bundle of bristles can be formed from individual active bristles.

A person skilled in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

What is claimed is:

1. An oral phototherapy apparatus comprising:
   a body sized and shaped so as to fit at least partially in a user's mouth; and
   at least one radiation emitting element coupled to the body to irradiate one or more regions of the oral cavity with phototherapeutic radiation;
   wherein the apparatus further comprises a motion sensor and controller which controls the at least one radiation emitting element based on signals from the motion sensor.

2. The apparatus of claim 1 wherein the apparatus further comprises first and second radiation emitting elements emitting light in first and second directions respectively.

3. The apparatus of claim 1 wherein the apparatus further comprises an optical element for directing radiation in different directions.

4. The apparatus of claim 1 wherein the apparatus is configured to direct radiation to at least one portion of the oral cavity selected from the group consisting of a tooth, cheek, tongue, palate, throat and facial tissue, lymphatic tissue, blood, gland, follicle, collagen and pigmentation.

5. The apparatus of claim 1 wherein the at least one radiating element further comprises at least two sources of radiation to be transmitted in different directions.

6. The apparatus of claim 1 wherein the at least one radiation emitting element further comprises a source of radiation having wavelength components in at least two separate spectral bands.

7. The apparatus of claim 1 wherein the at least one radiation emitting element further comprises at least two sources of radiation emitting different spectral bands of radiation.

8. The apparatus of claim 1 wherein the apparatus further comprises a controller for controlling at least one parameter for irradiation of the oral cavity selected from the group consisting of wavelength, power, pulsewidth and treatment time.

9. The apparatus of claim 1 wherein the at least one radiation emitting element further comprises at least one radiation source selected from the group consisting of light-emitting diodes, superluminescent diodes, laser diodes, vertical cavity surface emitting lasers, fiber lasers, fluorescent solid-state sources, and lamps.

10. The apparatus of claim 1 wherein the apparatus further comprises a plurality of bristles associated with the body.

11. The apparatus of claim 10 wherein the bristles are substantially transparent to phototherapeutic radiation within at least one wavelength range.

12. The apparatus of claim 10 wherein the bristles are coupled to the at least one radiation emitting element to receive and propagate radiation therefrom.

13. The apparatus of claim 10 wherein the bristles are at least partially coated with a reflective material.

14. The apparatus of claim 10 wherein the bristles have at least one shape, relative to an elongated direction of the bristles, selected from the group consisting of conical, tapered, curved and spiral shapes.

15. The apparatus of claim 10 wherein the bristles are shaped to transmit radiation upon contact between the bristles and a portion of the oral cavity 16. The apparatus of claim 10 wherein the bristles further comprise one or more fluorescent, luminescent or lasing elements.

17. The apparatus of claim 10 wherein the bristles are incorporated into a brush head, which is removable and replaceable.

18. The apparatus of claim 10 wherein the bristles are optically transmissive and coupled to at least one of the at least one radiation emitting element to receive and transmit radiation.

19. The apparatus of claim 18 wherein the light refractive characteristics of the optically transmissive bristles are selected to inhibit light transmission to the oral cavity in the absence of contact between the bristle and a surface of the teeth or cavity.

20. The apparatus of claim 1 wherein the apparatus further comprises a plurality of bristles and at least a portion of radiation from the at least one radiation emitting element is emitted in a direction which is not parallel to the bristles associated with the body.

21. The apparatus of claim 1 wherein the apparatus further comprises a contact sensor, wherein the controller controls the at least one radiation emitting element based on signals from the contact sensor.

22. The apparatus of claim 1 wherein the apparatus further comprises a diagnostic sensor, wherein the controller controls the at least one radiation emitting element based on signals from the diagnostic sensor.

23. The apparatus of claim 1 wherein the apparatus further comprises at least one thermally conductive element for extracting heat from the at least one radiating element.

24. The apparatus of claim 23 wherein the thermally conductive element comprises a fluid heat transfer medium.

25. The apparatus of claim 23 wherein the apparatus further comprises a handle that serves as a heat sink.

26. The apparatus of claim 23 wherein the thermally conductive element comprises a phase change material.

27. The apparatus of claim 23 wherein the apparatus further comprises a heat transfer element for heating a portion of the oral cavity with waste heat from the apparatus.

28. The apparatus of claim 1 wherein the apparatus further comprises a light diffuser optically coupled to the radiation emitting element to deliver diffuse radiation to the oral cavity.

29. The apparatus of claim 28 wherein said light diffuser comprises an optically transmissive element with a partially etched cladding.

30. The apparatus of claim 1 wherein the body is sized and shaped so as to fit at least partially in a user's mouth and adapted to conform to the shape of at least a portion of the oral cavity.

31. The apparatus of claim 30 wherein the body is compliant to facilitate conformation to a portion of the oral cavity.

32. The apparatus of claim 30 wherein the body is in the form of a mouthpiece adapted for positioning between at least a user's teeth and gums during phototherapy.

33. The apparatus of claim 30 wherein the body is adapted for placement in a position covering at least a portion of a user's lips during phototherapy.

34. The apparatus of claim 1 wherein the body is adapted for placement in a fixed position relative to the oral cavity during phototherapy.

35. The apparatus of claim 1 wherein the apparatus is configured such that, upon disposition of the apparatus within the mouth, radiation from the at least one radiating element can penetrate the mucosal lining of the oral cavity and deliver phototherapeutic energy to a region of facial tissue.

36. The apparatus of claim 1 wherein the apparatus further comprises an ultrasound generator for delivering acoustic energy to a target tissue site.

37. The apparatus of claim 1 wherein the apparatus further comprises a vibrating element for applying intermittent pressure to a target tissue site.

38. The apparatus of claim 1 wherein the apparatus further comprises a drug delivery port.

39. The apparatus of claim 1 wherein the apparatus further comprises an energy reflector for redirecting phototherapeutic radiation towards a target tissue site.

* * * * *